US010768166B2

(12) United States Patent
Galen et al.

(10) Patent No.: US 10,768,166 B2
(45) Date of Patent: Sep. 8, 2020

(54) DIAGNOSTICS SYSTEMS AND METHODS

(71) Applicant: HEMEX HEALTH, INC., Portland, OR (US)

(72) Inventors: Peter Galen, Portland, OR (US); David John Sayler, Portland, OR (US); Joshua King Hoyt, Portland, OR (US); Daniel E. Grupp, Portland, OR (US); Brian T. Grimberg, Shaker Heights, OH (US); Umut Atakan Gurkan, Shaker Heights, OH (US)

(73) Assignee: Hemex Health, Inc., Portland, OR (US)

( * ) Notice: Subject to any disclaimer, the term of this patent is extended or adjusted under 35 U.S.C. 154(b) by 0 days.

(21) Appl. No.: 15/599,368

(22) Filed: May 18, 2017

(65) Prior Publication Data
US 2018/0067101 A1 Mar. 8, 2018

Related U.S. Application Data

(60) Provisional application No. 62/385,146, filed on Sep. 8, 2016.

(51) Int. Cl.
*G01N 33/49* (2006.01)
*G01N 35/00* (2006.01)
(Continued)

(52) U.S. Cl.
CPC ......... *G01N 33/49* (2013.01); *A61B 5/15003* (2013.01); *A61B 5/15103* (2013.01);
(Continued)

(58) Field of Classification Search
CPC .................. G01N 33/49; G01N 21/84; G01N 2035/00891; B01L 3/502; B01L 2300/0672; B01L 2400/043; B01L 2300/0654
See application file for complete search history.

(56) References Cited

U.S. PATENT DOCUMENTS 5,069,769 A  12/1991  Fujimiya et al.
5,108,754 A   4/1992  Wilburn
(Continued)

FOREIGN PATENT DOCUMENTS

JP   2002-328113   11/2002
JP   2004-069430    3/2004
(Continued)

OTHER PUBLICATIONS

Petra Laboratory evaluation on the sensitivity and specificity of a novel and rapid detection method for malaria diagnosis based on magneto-optical technology (MOT) Mens et al. Malaria Journal 2010, 9:207.*
(Continued)

*Primary Examiner* — Samuel P Siefke
(74) *Attorney, Agent, or Firm* — Lane Powell PC

(57) ABSTRACT

A point-of-care diagnostic system that includes a cartridge and a reader. The cartridge can contain a patient sample, such as a blood sample. The cartridge is inserted into the reader and the patient sample is analyzed. The reader contains various analysis systems, such as a magneto-optical system that measures a light transmission differential through the patient sample in varying magnetic fields. The reader can process data from the various patient sample analysis to provide interpretative results indicative of a disease, infection and/or condition of the patient.

45 Claims, 11 Drawing Sheets

(51) Int. Cl.

| | | |
|---|---|---|
| *G01N 33/487* | (2006.01) | |
| *G01N 21/84* | (2006.01) | |
| *A61B 5/15* | (2006.01) | |
| *A61B 5/151* | (2006.01) | |
| *G01N 21/17* | (2006.01) | |
| *B01L 3/00* | (2006.01) | |

(52) U.S. Cl.
CPC .. *A61B 5/150633* (2013.01); *A61B 5/150755* (2013.01); *G01N 21/1717* (2013.01); *G01N 21/84* (2013.01); *G01N 33/48792* (2013.01); *G01N 35/00871* (2013.01); *B01L 3/502* (2013.01); *B01L 2200/0684* (2013.01); *B01L 2200/143* (2013.01); *B01L 2300/0654* (2013.01); *B01L 2300/0672* (2013.01); *B01L 2400/043* (2013.01); *B01L 2400/0481* (2013.01); *G01N 2021/1727* (2013.01); *G01N 2035/00881* (2013.01); *G01N 2035/00891* (2013.01); *G01N 2333/445* (2013.01); *G01N 2800/26* (2013.01)

(56) References Cited

U.S. PATENT DOCUMENTS

| | | | |
|---|---|---|---|
| 5,202,006 | A | 4/1993 | Chen |
| 5,827,681 | A | 10/1998 | Krug et al. |
| 5,978,694 | A | 11/1999 | Rapoport et al. |
| 6,818,185 | B1 * | 11/2004 | Petersen ............... B01L 3/502 |
| | | | 422/130 |
| 7,639,359 | B2 | 12/2009 | Chung et al. |
| 8,214,006 | B2 | 7/2012 | Newman et al. |
| 8,423,104 | B2 | 4/2013 | Wiseman et al. |
| 9,632,077 | B2 * | 4/2017 | Hirase ............... G01N 33/54326 |
| 9,697,556 | B2 * | 7/2017 | Mazed ................... G06Q 30/02 |
| 2001/0012612 | A1 * | 8/2001 | Petersen ............... B01L 3/502 |
| | | | 435/5 |
| 2002/0012902 | A1 | 1/2002 | Fuschs et al. |
| 2002/0042125 | A1 * | 4/2002 | Petersen ........... B01L 3/502715 |
| | | | 435/287.2 |
| 2002/0086416 | A1 | 7/2002 | Sato et al. |
| 2004/0173456 | A1 | 9/2004 | Boos et al. |
| 2004/0256230 | A1 | 12/2004 | Yager et al. |
| 2005/0020893 | A1 | 1/2005 | Diab |
| 2006/0013740 | A1 | 1/2006 | Berndtsson et al. |
| 2006/0025659 | A1 | 2/2006 | Kiguchi et al. |
| 2007/0059204 | A1 | 3/2007 | Witty et al. |
| 2007/0284250 | A1 | 12/2007 | Magnant et al. |
| 2008/0227209 | A1 | 9/2008 | Deng |
| 2009/0314641 | A1 | 12/2009 | Rooney et al. |
| 2009/0318784 | A1 | 12/2009 | Newman et al. |
| 2010/0010858 | A1 | 1/2010 | Matoba |
| 2010/0147688 | A1 | 6/2010 | El Hadidy |
| 2010/0149519 | A1 | 6/2010 | Toofan et al. |
| 2010/0181199 | A1 | 7/2010 | Sugiyama |
| 2010/0307921 | A1 | 12/2010 | Frazier |
| 2011/0065209 | A1 * | 3/2011 | Heil ................. G01N 33/54326 |
| | | | 436/501 |
| 2011/0104738 | A1 | 5/2011 | Forsell |
| 2011/0196222 | A1 | 8/2011 | Behrend et al. |
| 2011/0244467 | A1 | 10/2011 | Haswell |
| 2012/0012462 | A1 | 1/2012 | Sugiyama |
| 2012/0021456 | A1 | 1/2012 | Levine et al. |
| 2012/0257199 | A1 | 10/2012 | Liu et al. |
| 2012/0326104 | A1 | 12/2012 | Kwon et al. |
| 2014/0004501 | A1 | 1/2014 | Talebpour et al. |
| 2015/0064693 | A1 * | 3/2015 | Khattak ........... G01N 33/54366 |
| | | | 435/5 |
| 2015/0125873 | A1 | 5/2015 | Newman et al. |
| 2015/0377857 | A1 * | 12/2015 | Grimberg ............... G01N 21/21 |
| | | | 356/39 |
| 2016/0066754 | A1 | 3/2016 | Haegermarck |
| 2016/0116439 | A1 | 4/2016 | Kindwall et al. |
| 2017/0108495 | A1 * | 4/2017 | Ikeda ............... G01N 33/54333 |

FOREIGN PATENT DOCUMENTS

| | | | |
|---|---|---|---|
| JP | 2005-538381 | | 12/2005 |
| JP | 2006-064398 | | 3/2006 |
| JP | 2016024021 | | 2/2016 |
| WO | WO9633410 | | 7/2010 |
| WO | WO2010141921 | | 12/2010 |
| WO | WO2013071301 | | 5/2013 |
| WO | 2016066754 | * | 5/2016 |
| WO | WO2016066754 | | 5/2016 |

OTHER PUBLICATIONS

Search Report and Written Opinion for Singapore Patent Application No. 112017007331.
International Preliminary Report on Patentability dated Jan. 31, 2017, International Application No. PCT/US2015/042907, International filing date.
Written Opinion dated Jan. 7, 2016, International Application No. PCT/US2015/042907, International filing date.
International Search Report dated Jan. 7, 2016 International Application No. PCT/US2015/042907, International filing date.
Nov. 7, 2017 Written Opinion, International Application No. PCT/US2017/50809, International filing date Sep. 8, 2017.
International Search Report dated Nov. 7, 2017, International Application No. PCT/US2017/50809, International filing date Sep. 8, 2017.
International Search Report dated Sep. 29, 2017, International Application No. PCT/US20174/033409, International filing date Jun. 15, 2017.
Written Opinion dated Sep. 29, 2017, International Application No. PCT/US2017/033409, International filing date May 18, 2017.
Web Page: "http://www.tedxcle.com/dr-brian-grimberg/"; Published Jan. 3, 2013; viewed May 10, 2018.
Tang et al.: "Hemoglobin electrophoresis", Clinical Immunology newsletter, Elsevier, US. vol. 13, No. 8, Aug. 1, 1993.
EPO Search Report, dated Jan. 30, 2018, EPO Appl. No. 15827038.9; pp. 1-8.
Notice of Allowance dated Jun. 5, 2017, U.S. Appl. No. 15/425,729, filed Feb. 6, 2017.
Notice of Allowance dated Feb. 28, 2017, U.S. Appl. No. 15/425,729, filed Feb. 6, 2017.
Notice of Allowance dated Dec. 2, 2016, U.S. Appl. No. 14/766,523, filed Aug. 7, 2015.
Amendment filed Oct. 20, 2016, U.S. Appl. No. 14/766,523, filed Aug. 7, 2015.
Non-Final Rejection dated Oct. 7, 2016, U.S. Appl. No. 14/766,523, filed Aug. 7, 2015.
Notice of Allowance dated Jun. 8, 2016, U.S. Appl. No. 14/766,523, filed Aug. 7, 2015.
Preliminary Amendment filed Jan. 15, 2016, U.S. Appl. No. 14/766,523, filed Aug. 7, 2015.
International Search Report dated May 14, 2014, International Application No. PCT/US2014/015604, International filing date Feb. 10, 2014.
Written Opinion dated May 14, 2014, International Application No. PCT/US2014/015604, International filing date Feb. 10, 2014.
International Preliminary Report on Patentability dated Aug. 11, 2015, International Application No. PCT/US2014/015604, International filed Feb. 10, 2014.
Kohn J. Separation of hemoglobins on cellulose acetate. J. Clin Pathol., Jan. 31, 1969, vol. 22, No. 1, pp. 109-111.
Graham J. L. Grunbaum B. W., A rapid method for microelectrophoresis and quantitation of hemoglobins on cellulose acetate. Am J Clin Pathol., Jun. 30, 1963, vol. 39, No. 6, pp. 567-578.
Hemechip for Early Diagnosis of Sickle Cell Disease. Jul. 1, 2014, https://contest.techbriefs.com/2014/entries/medical5025.
Protocol: Cellulose acetate electrophoresis. Sep. 17, 2013, http://web.archive.org/web/20130917003807/http://www.ithanet.eu:80/ithapedia/index.php/protocol:cellulose_acetate_electrophoresis.
Grimberg B., "Manipulations of Malaria Parasies With Magnets" p. 1-102, Jan. 27, 2012, CWRU, World Health Interest Group Meeting, Cleveland, OH.

(56) References Cited

OTHER PUBLICATIONS

Mens, Petra F., et al. "Laboratory evaluation on the sensitivity and specificity of a novel and rapid detection method for malaria diagnosis based on magneto-optical technology (MOT)." Malaria journal 9.1 (Published Jul. 19, 2010).
Chung et al.; Magneto-optic measurement of Brownian relaxation nanoparticles; Journal of Magnetism and Magnetic Materials 320; 2008, pp. 91-95.
Feb. 7, 2018 Amendment, U.S. Appl. No. 15/699,962, filed Sep. 8, 2017.
Jan. 30, 2017 Preliminary Amendment dated Jan. 30, 2017, U.S. Appl. No. 15/500,447, filed Jan. 30, 2017.
May 19, 2018 Notice of Allowance, U.S. Appl. No. 15/699,962, filed Sep. 8, 2017.
International Preliminary Report on Patentability mailed dated Mar. 12, 2019, International Application No. PCT/US2017/50809, International filing date Sep. 8, 2017.
International Preliminary Report on Patentability dated Mar. 12, 2019, International Application No. PCT/US2017/033409, International filing date May 18, 2017.
Old et al. (Chapter 3 of Prevention of Thalassaemias and Other Haemoglobin Disorders: vol. 2: Laboratory Protocols, 2nd edition, Haemoglobin pattern analysis) (Year: 2012).
Feb. 6, 2019 Notice of Allowance, U.S. Appl. No. 15/699,962, filed Sep. 8, 2017.
NonFinal Office Action mailed, U.S. Appl. No. 15/500,447, filed Jan. 30, 2017.
Office Action for Chinese Patent Application No. 201580052224.X, dated Nov. 22, 2018.
Office Action for Japanese Patent Application No. 2017-505197, dated Jan. 22, 2019.
Feb. 25, 2019 Amendment, U.S. Appl. No. 16/113,261, filed Aug. 27, 2018.
Mar. 29, 2019 Notice of Allowance, U.S. Appl. No. 16/113,261, filed Aug. 27, 2018.
First Examination Report dated Jun. 4, 2019, Indian Application No. 2019017013514.
First Examination Report dated May 31, 2019, Indian Application No. 2019017013517.
Office Action dated Aug. 22, 2019 in U.S. Appl. No. 16/512,122, filed Jul. 15, 2019.
UNG, "The Design Fabrication, and Testing of a Point-of-Care Device for Diagnosising Sickle Cell Disease and Other Hemoglobin Disorders", May 2016, XP055679567, Rerived from the internet: URL: https://etd.ohiolink.edu/!etd. send_file?accession= case1459188452&disposition= inline.
Partial Supplementary European Search report dated Mar. 31, 2020 for European Application No. EP17849235.1.
Extended European Search Report dated Apr. 6, 2020 for European Application No. 17849672.5.

* cited by examiner

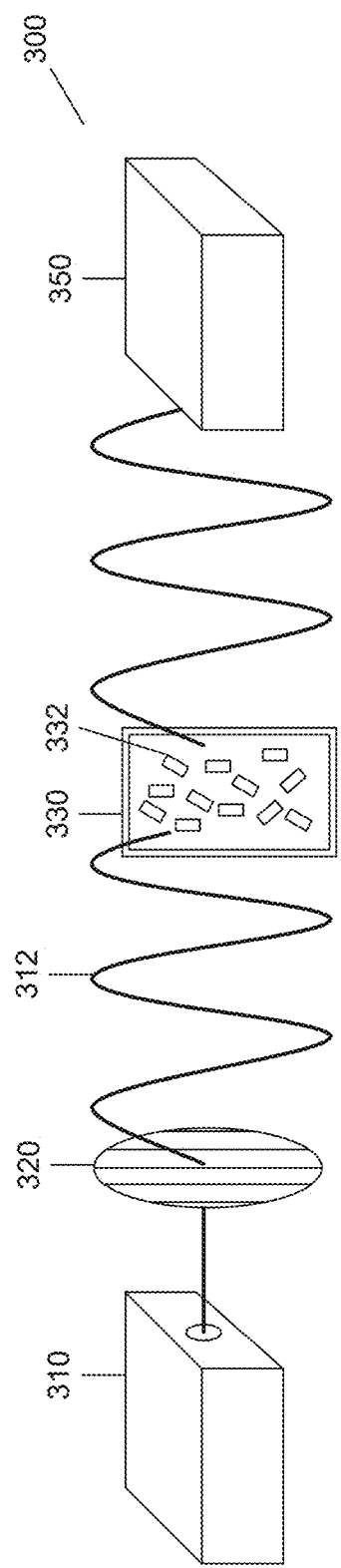
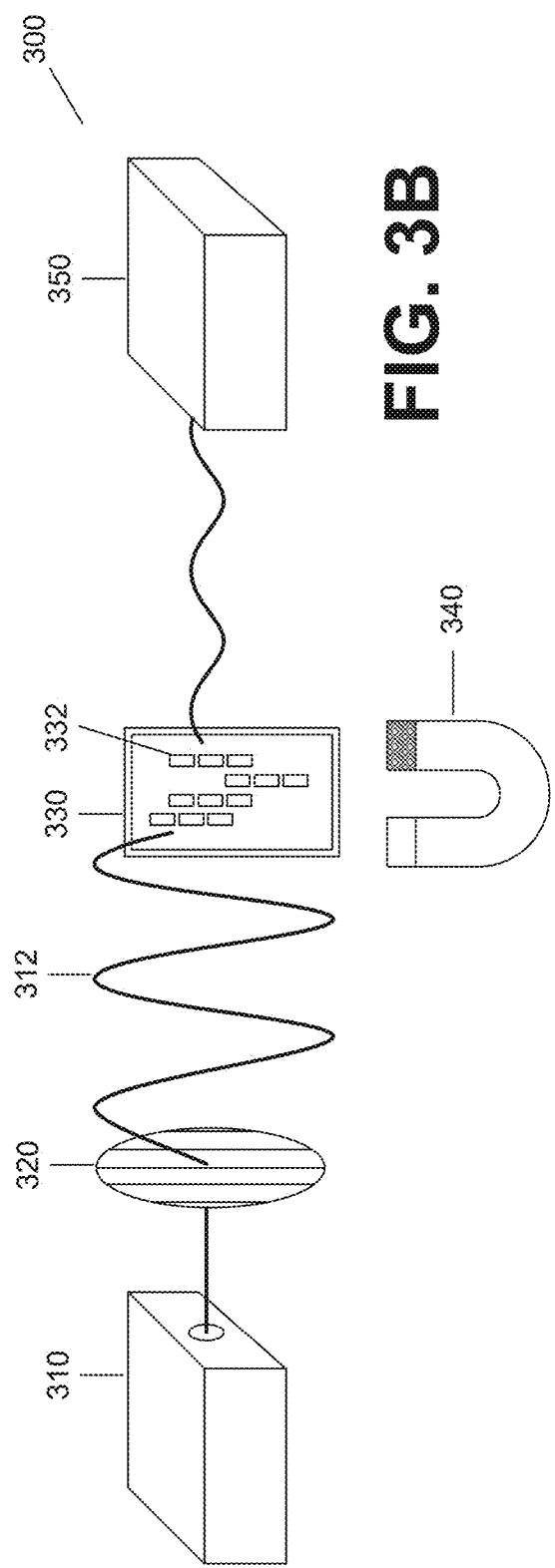

DIAGNOSTICS SYSTEMS AND METHODS

CROSS-REFERENCE TO RELATED APPLICATIONS

This application claims priority to U.S. Provisional Patent Application Ser. No. 62/385,146, filed Sep. 8, 2016, the contents of which are herein incorporated by reference in their entirety.

BACKGROUND

Patient diagnostic services save lives, they reduce the time to treatment for the patient and provide valuable insight for targeted treatment. In many developed countries, modern medical facilities can provide patients with the most advanced diagnostic services allowing patients to be efficiently and effectively treated. In less developed countries or regions, high quality medical facilities and diagnostic services can be lacking, often due to economic and infrastructure considerations. In many less developed countries, the economy cannot afford the latest in medical technology and infrastructure, such as a robust power grid or highly trained clinicians, required to support the high demands of modern medical technology. Sadly, a large portion of the world's population resides in underserved or developed areas where the lack of efficient and effective diagnostic services critically impacts the population mortality and overall health. This lack of medical care can lead or contribute to knock-on effects, such as low economic and education development, which can further hamper the populace.

Less developed countries and areas lack significant diagnostic services that could shorten treatment and increase the living standard of the population. Many of the diseases and conditions the populations of less developed countries and areas face have largely been extinguished in developed countries, which means the treatment exists, may be plentiful, and may be, in some cases, relatively low cost for these diseases and conditions. The component that is lacking is the diagnostic services to diagnose members of the population effectively and efficiently so that they can receive prompt, timely treatment, which minimizes the impact of the disease or condition on the patient and the population.

Often, many less developed countries and areas also lack the educational development that is typically required to perform the necessary diagnostic services. This can lead to inconclusive or erroneous results from diagnostic services or to significant delays in diagnosis as the diagnostic services are required to be performed in another location that has the requisite infrastructure and/or knowledge to perform the diagnostic service. For patients, this can mean further delays in treatment, which can decrease their chances of survival, increase the spread of the disease, and/or lead to increased debilitation caused by the disease or condition.

One of the common diseases effecting less developed countries and areas is malaria, a disease caused by a mosquito-borne parasite, plasmodium. Malaria infects many people each year, disproportionately in less developed countries and areas than developed ones. Malaria, if identified at an early stage of the infection, can be easily treated with relatively low cost treatment plans, but without early diagnosis, the disease causes great harm to individual patients, it quickly spreads among a population, and later-stage treatment is often costly and less effective. The populations most effected by malaria are vulnerable and do not have good access to quality and timely diagnostic services. Further, the malaria disease is very treatable if timely detected or diagnosed, however, the diagnostic services needed are often not readily and/or easily available in the countries and areas in which malaria is endemic.

Many countries effected by malaria and many humanitarian aid groups have directed resources and technology to malaria control and reducing and managing the disease and others like it. These resources and technology attack malaria on two fronts, the control of mosquitoes and the treatment and diagnosis of the disease. The current gold standard diagnostic services used to diagnose malaria, such as polymerase chain reaction (PCR) based tests, are expensive and require sophisticated laboratory analysis, and point-of-care blood films (light microscopy) and antigen-based rapid diagnostic tests (RDTs) lack the necessary sensitivity and speed to provide the necessary information to optimally treat malaria.

A low-cost, accurate, point-of-care in vitro diagnostic service or device that can effectively and efficiently diagnose biologic fluid disease, conditions or ailments would greatly benefit many countries and areas, from those that are developed to those that are less developed. The efficient and effective diagnosis of disease, conditions, or ailments can have great impacts on individual patients and populations.

BRIEF DESCRIPTION OF THE DRAWINGS

FIGS. 3A-3B illustrate an example magneto-optical detection system.

DETAILED DESCRIPTION

Various example point-of-care, in vitro diagnostic devices and methods for detecting and helping to diagnose infections, diseases and/or conditions, such as a parasitic infection, are described herein. The disclosed diagnostic devices include a cartridge and reader that interface to analyze a patient biologic sample, such as a blood sample, to provide a diagnosis, or patient biologic sample data regarding one or more diseases or conditions of the patient. A magneto-optical system, an electrophoresis system and/or further in vitro diagnostic and/or patient biologic sample analysis systems can be included in the reader and cartridge to diagnose and/or provide patient biologic sample data regarding a variety of diseases or conditions. The cartridge and reader provide an economic, efficient, and effective point-of-care diagnostic system. The biologic sample could be the patient's blood, saliva, urine, or other fluid, a liquid suspension of tissue, or a combination of fluids. Many of the examples discussed here explain the systems and methods of analyzing a patient blood sample, but it is understood that any biologic sample could be used.

Figure 1:
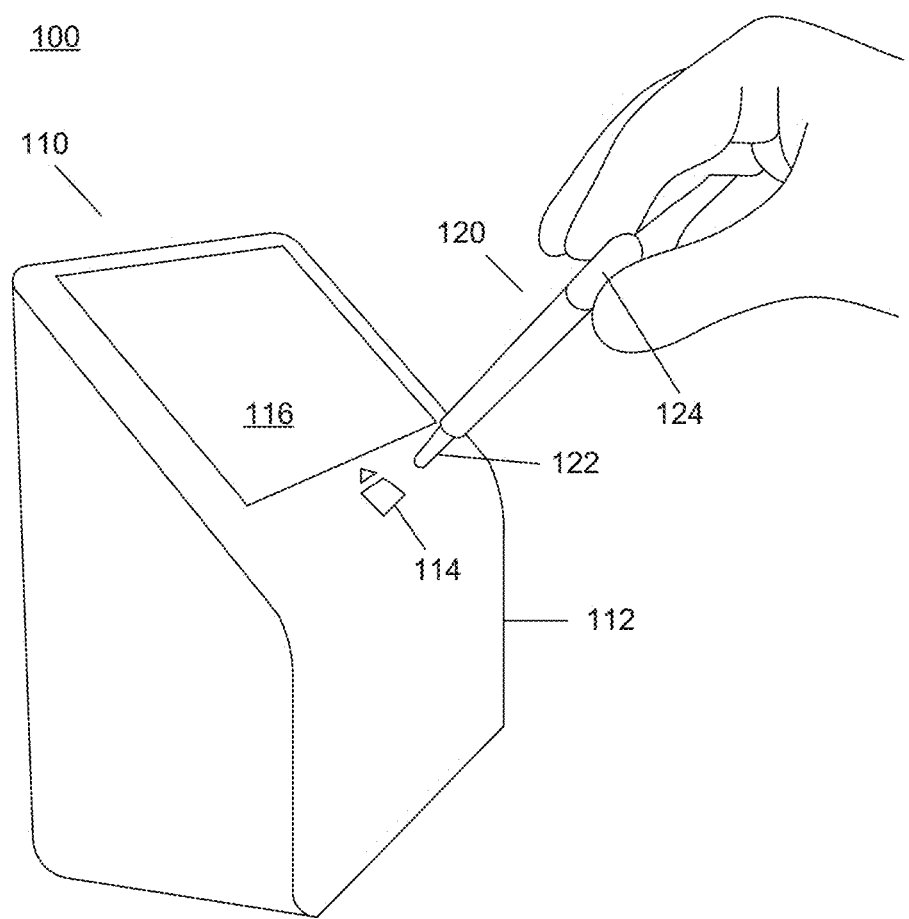
FIG. 1 illustrates an example diagnostic system.

FIG. 1 illustrates an example reader 110 and cartridge 120 of a point-of-care blood diagnostic system 100. A point-of-care blood diagnostic systems includes devices that are physically located at the site at which patients are tested and sometimes treated to provide quick results and highly effective treatment. Point-of-care devices can provide information and help in diagnosing patient infections while the patient is present with immediate referral or treatment determined and administered immediately. Unlike gold standard laboratory-based blood testing for infections, the disclosed point-of-care devices are highly sensitive, efficient, and effective in aiding early treatment of disease.

The reader 110 includes a housing 112, a cartridge receptacle 114 and a display 116. The cartridge 120, which contains the patient sample and, optionally dilutants and/or reagents, is inserted into the cartridge receptacle 114 of the reader 110 to transfer the patient sample, treated or untreated, into the reader 110 to perform a diagnostic test or analysis. The cartridge 120 can include a pipette-like end 122 and a bulb 124 for siphoning a patient sample into the cartridge 120 in preparation for the diagnostic test. Alternatively, the cartridge 120 can include a capillary tube by which the patient sample can be obtained for analysis and/or testing.

The housing 112 of the reader 110 can be constructed of materials such as plastic or metal and is preferably sealed with a smooth surface, which allows the reader 110 to be easily cleaned and/or disinfected and resist external water and or dust. Further, the housing 112 is sufficiently strong to allow the safe transport and use of the reader 110 without substantial damage to the reader 110 and the diagnostic systems within. Additionally, the housing 112 can have properties, which shields or minimizes the exposure of the interior of the reader 110 to temperature and/or humidity variations and/or light intrusion. The robustness of the reader 110 allows it to be used in a variety of locations and environments without adversely affecting the results of the diagnostic system.

The housing 112 of the reader 110 can also include vibration isolation to prevent vibration of the reader 110 during the measurement process to assist with preventing analysis error of the patient sample. Vibration isolation can include suspending and/or isolating the components and/or systems of the reader 110 within the housing 112 or containing the components and/or systems within an internal housing that is suspended and/or isolated from the external housing 112. Alternative vibration isolation can include anti-vibration feet or mounts on which the reader 110 can sit on a surface. Additional vibration isolation can include placing the reader 110 on a cushioned and/or anti-vibration mat to reduce or limit the vibration and/or disturbance of the reader 110 by its external environment.

The cartridge receptacle 114 can be conformably shaped to receive the cartridge 120. The cartridge 120 can be received partially or completely into the cartridge receptacle 114 or the reader 110. Alternatively, the cartridge 120 can be otherwise connected, such as by an external receptacle or conduit, to the reader 110 to transfer the patient sample, or portion thereof, into the reader 110. Such an external receptacle or conduit can be electrically coupled to the electronics housed in the reader 110 by a wireless or hard-wire connection of any suitable configuration.

Figure 2A:
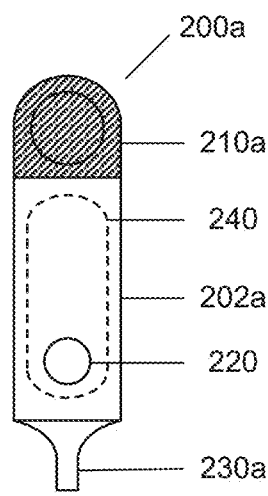
FIGS. 2A-2B illustrate example cartridges.
Figure 2B:
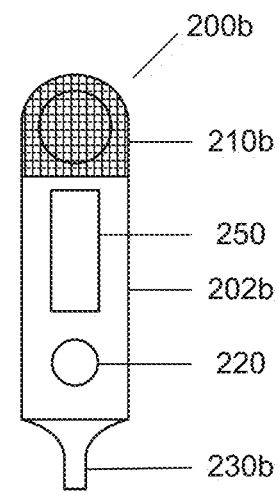

FIGS. 2A-2B illustrate example cartridges 200a and 200b. Each of the example cartridges 200a, 200b include a housing 202a. 202b an upper portion 210a, 210b and a lower portion 230a, 230b. The cartridges 200a, 200b can include a sample chamber, such as 240 of FIG. 2a, that is internal to the cartridge 200a. 200b and can store a patient sample, such as a blood sample, within the cartridge 200a, 200b. The cartridges 200a, 200b transport or store a patient sample for analysis, or reading, by a reader. Further, the cartridges 200a, 200b can interface with the reader to assist with or facilitate the reading or analysis of the patient sample stored within the cartridge 200a, 200b. That is, the cartridge 200a, 200b can include features, such as an optical window 220 and an electrophoresis element 250 of cartridge 200b of FIG. 2B to assist with the analysis of the patient sample within the cartridge 200a, 200b. The cartridge 200a, 200b can also transfer all or a portion of the patient sample to the reader for analysis of the patient sample. The patient sample, or portion thereof, from the cartridge 200a, 200b can be transferred to a blood sample chamber of the reader or to another location of the reader, or external from the reader, for analysis of the patient blood sample.

The cartridges 200a. 200b can be disease, condition and/or ailment specific or multiple disease, condition and/or ailment specific. The cartridges 200a, 200b can include various features, external and/or internal, that customize a particular cartridge for the analysis of a specific, singular or multiple, disease, condition and/or ailment. The cartridge specificity can include the patient sample size volume of the cartridge, various dilutants and/or reagents in the cartridge, the interface of the cartridge with the reader and other design and/or construction specification of the cartridge in relation to one or more particular diseases, conditions and/or ailments.

The housing 202a, 202b of the cartridge 200a. 200b can include structural, material and/or geometric features that assist or facilitate the analysis and/or acquisition of the patient sample. Such features can include internal chambers, such as the sample chamber 240 of FIG. 2A, to store the patient sample or other fluids or compounds, that are sized to ensure adequate sample size for the analysis of the collected patient blood sample, interfaces that interact with, engage, or facilitate the systems of the reader during analysis of the patient sample. Other features can include environmental controls that maintain the collected patient sample in a suitable condition for analysis, and other features and/or considerations. For example, an internal chamber of the reader could manually or automatically interface with the inserted cartridge via a port to cause dilutants and other chemical treatments to mix with the patient sample in the cartridge. Such a port would be a passage, like a tube, that connects the sample chamber of the cartridge with the port so fluids can be added to the cartridge. The additional of such external fluids can be triggered manually when a user actuates a switch or other actuator, which the user may do in response to a user prompt to do so. The cartridge housing 202a, 202b can be formed of a suitable material such as a plastic, composite and/or metal to create a robust, disposable cartridge 200a, 200b. Additionally, the housing 202a, 202b material can be selected for the ability to be sterilized, such as sterilizing the cartridge 200a, 200b prior to use, for reuse or for killing pathogens prior to disposal.

Environmental considerations can also be used in the determination of a suitable cartridge 200a, 200b housing 202a, 202b material(s). Such environmental considerations can include the biodegradability of the housing material, the recyclability of the housing material, the incineration by-products of the housing material and other environmental considerations. These environmental considerations can reduce the environmental impact of the disposal, recycling and/or reuse of the cartridges 200a. 200b after use.

The housing 202a, 202b of the cartridge 200a, 200b can include a patient identification marker or an area to apply or mark patient identification onto the cartridge 200a, 200b. This marker could be in machine readable or human readable form or both. The patient identification allows the correlation of the analysis of the collected patient sample with a particular patient. Additionally, the reader can detect the patient identification marker to correlate the analysis with a patient, including automatically appending the analysis results to a patient's medical records. In an example embodiment, the patient identification can be obfuscated to remove patient personal information, such as a name, from the cartridge 200a, 200b, instead the patient can be assigned a random number, or sequence of characters, that is correlated to the particular patient in the reader, a computer or other system.

Patient diagnostic and demographic information can also be used for analysis to determine outbreaks, trends or emergence of diseases, conditions, or ailments. This analysis can be used to prevent or minimize the spread of the disease and/or targeted treatment of the condition. For preventable conditions, such as a mosquito-borne disease like malaria, geographical correlation of the prevalence of the condition can be used to perform preventative measures to mitigate and minimize the condition and spread thereof.

The upper portion 210a, 210b of the cartridge 200a, 200b can include an identification marker, such as a color, pattern, name, or other distinguishing feature. The identification marker can be used to indicate the use of the cartridge 200a. 200b for the analysis of a specific disease or diseases, condition(s) and/or ailment(s). This can provide a clear, visual indication to a user that the cartridge 200a, 200b is to be used with specific analysis or analyses.

Additionally, the upper portion 210a, 210b can be a portion of a sample collection element, such as a suction bulb, actuation element, or capillary tube to assist or facilitate the collection of the patient sample into the cartridge 200a. 200b. As a suction bulb, the upper portion can be formed of a resilient or flexible material capable of deforming in volume to assist in the uptake of a patient sample within the cartridge 200a, 200b. As an actuation element, the application of pressure or other input by a user, other or device to the upper portion 210a, 210b of the cartridge 200a, 200b can actuate the passive or active acquisition of a patient sample into the cartridge 200a, 200b in preparation for analysis, such as extending and/or retracting a needle or capillary tube. A capillary tube is one means of passively collecting the sample with no user or machine pressure required.

Further, the upper portion 210a, 210b can contain a dilutant, reagent or other fluid or substance that is stored internally in a chamber and that can be released into and/or mixed with the patient sample within the cartridge 200a, 200b. Application of pressure to the upper portion 210a, 210b of the cartridge 200a, 200b can introduce the contained substance or fluid into the patient sample within the cartridge 200a, 200b which mixes the patient sample with the contained substance or fluid. Example dilutant ratios can include from 1:1 to 1:100. The contained substance or fluid can assist with the analysis of the patient sample, preparation of the patient sample for analysis, preservation of the sample for analysis or other desirable or necessary patient sample modification for efficient and effective analysis of the patient sample.

Additionally, the upper portion 210a, 210b of the cartridge 200a. 200b can be contoured and/or shaped to provide a comfortable, ergonomic, and/or easy grip for a user to handle the cartridge 200a, 200b during insertion and/or extraction into/from the reader or diagnostic device. Alternatively, the surface texture of the upper portion 210a, 210b can be such that it provides similar gripability for a user during handling of the cartridge 200a, 200b.

The optical window 220 can be included on the cartridge 200a, 200b, which allows light to pass into and/or through a portion of the cartridge 200a, 200b such as a sample chamber containing the patient sample, such as 240 of FIG. 2A. The ability to pass light into and/or through the sample volume within the cartridge 200a, 200b can be a necessary step during analysis of the patient sample within the cartridge 200a. 200b. The optical window 220 can be a material and/or construction that necessarily or desirably alters light entering the optical window 220 as a part of the analysis of the patient sample within, such as collimating, filtering, and/or polarizing the light that passes through the optical window 220. Alternatively, the optical window 220 can be transparent or translucent, or can be an opening within the housing 202a, 202b of the cartridge 200a, 200b. The cartridge 200a, 200b can include a reflector opposite the optical window 220, 220b that reflects the incoming light back through the optical window 220a, 220b or through another optical window, or can include a further optical window opposite the light entry window to allow light to pass through the cartridge 200a, 200b.

An electrophoresis element, such as 250 of cartridge 200b of FIG. 2B, can assist with performing an electrophoresis analysis of a patient sample within the cartridge 250. The electrophoresis element 250 can include electrodes to establish an electrical gradient across the element to perform the electrophoresis analysis.

The lower portion 230a, 230b can house or be a portion of the sample collection system. In the examples shown in FIGS. 2A and 2B, the lower portion 230a, 230b can include a channel or tube through which the patient sample can be transferred into the interior of the cartridge 200a, 200b. The lower portion 230a, 230b can also house a portion of the sample collection system, such as an extendable needle like a lancet or a capillary tube through which the patient sample can be transferred to the interior of the cartridge 200a, 200b.

The lower portion 230a, 230b can also include elements and/or systems to assist with the analyzation and/or storage of the patient sample. This can include an interface and/or mechanism to release at least a portion of the patient sample from within the cartridge 200a, 200b into the reader and/or a barrier or seal that restrains and/or preserves the patient sample within the cartridge 200a, 200b.

The lower portion 230a, 230b can further include an indicator that is visible once the cartridge 200a, 200b has been previously used. This can prevent cross-contamination of patient specimens and/or prevent the reuse of a single-use cartridge 200a, 200b which could alter or otherwise compromise the results of the patient sample analysis. The indication can be structural in nature, with an alteration, such as a removal or break in a portion of the cartridge 200a, 200b housing 202a. 202b of the lower portion 230a. 230b that is a visible once the cartridge 200a, 200b has been used or has acquired a patient sample. Additionally, the lower portion 230a, 230b can deform after acquisition of a patient sample within the cartridge 200a, 200b, which prevents further collection of a patient sample(s) using the cartridge 200a. 200b. The indication could be electrical.

FIGS. 3A-3B illustrate an example magneto-optical detection (MOD) system 300. The MOD system 300 includes a light source 310 that emits light 312, a polarizer 320, a patient sample 330, a magnet 340 and a photodetector

350. Some diseases and conditions result in the release of or changes in a magnetic, or paramagnetic, component of a patient's sample. An example patient sample can include blood which includes hemozoin, that contains iron—a magnetic compound, the amount and/or concentration of which can be used to determine the presence and/or intensity of a condition or disease, such as malaria. The transmission of light 312 through a patient sample 330 in a varying magnetic field can be used to detect the presence of and determine, absolute and/or relative, concentrations of magnetic and non-magnetic components within the patient sample 330.

FIG. 3A illustrates the transmission of light 312, from the light source 310, through the patient sample 330 in a magnetic field in a first state, such as a low strength magnetic field. In this example, a magnetic component 332 of the patient sample 330 is randomly arranged allowing for a measurable transmittance of light 312 through the patient sample 330. The transmitted light 312 is received by the photodetector 350 and characterized, such as by properties including frequency, intensity, distribution, wavelength and/or other light properties or characteristics. This first light value is a base value that can be used to measure the relative change in at least a property or characteristic of the light transmitted through the patient sample 330 with an alternate, varying or changeable magnetic field applied.

FIG. 3B illustrates the transmission of light 312, from the same light source 310, through the patient sample 330 in the presence of an applied magnetic field in a second state, such as a higher strength magnetic field than the first state. The strength of the magnetic field applied to the patient sample 330 can be increased from the first state to the higher strength second state by altering the proximity of a magnet 340. The application of a higher strength magnetic field causes the ordered alignment or arrangement of the magnetic, or paramagnetic, components 332 of the patient sample 330. This ordering or alignment effects the transmission of light 312 through the patient sample 330, which is a second value that can be detected by the photodetector 350. An effect can include the reduction or increase of light 312 transmitted through the patient sample 330. The comparison and/or measurement of the first light value in a magnetic field in a first, lower, state, and the second light value in a magnetic field in a second, higher, state, can be used to determine the presence of a disease or condition and/or the intensity of the disease or condition, such as the level of infection.

An example disease detectable by an MOD system, such as that of FIGS. 3A-3B, can include malaria. Malaria can be caused by a variety of different plasmodium parasites which infect the hemoglobin containing red blood cells of a host. The plasmodium replicate within the red blood cells, eventually destroying the red blood cells. The plasmodium parasite(s) release hemozoin as a byproduct after having digested an infected patient's healthy hemoglobin. Hemozoin in a patient's blood is a biomarker of malaria. Hemozoin is a paramagnetic compound and is thus sensitive to magnetic fields. Hemozoin within a patient sample can be detected by an MOD system due to a differential light transmission characteristic(s) in different magnetic fields. The differential light transmission characteristic can be indicative of several infection characteristics, such as the presence of the parasite, the parasite infection levels, the parasite species, and other infection characteristics.

An MOD system, such as the example of FIGS. 3A-3B, can be integrated into a reader, such as the example shown in FIG. 1, or can be external to a reader. In the example in which the MOD system is external to a reader, the MOD system requires the ability to pass light through the patient sample, within a cartridge or reader, and detect properties and/or characteristics of the light transmitted through the patient sample in a varying/changeable magnetic field. Alternatively, the MOD system and components can be split between the reader and external to the reader, with a portion of the MOD system and/or components located internal to the reader and another portion of the MOD system and/or components located external to the reader.

Additionally, an example MOD system can include only the optical component. Light from a light source is transmitted through a patient sample and the transmitted light is received by a light detector that can determine and/or measure properties/characteristics of the transmitted light or can transmit information from which the properties/characteristics of the transmitted light can be determined or measured. In this example, the magnetic component of the MOD system is either absent from the system or is not used during analysis of a patient sample. Instead, the patient sample can be analyzed based on the light transmission differential and/or characteristics of the transmitted light.

Figure 4:
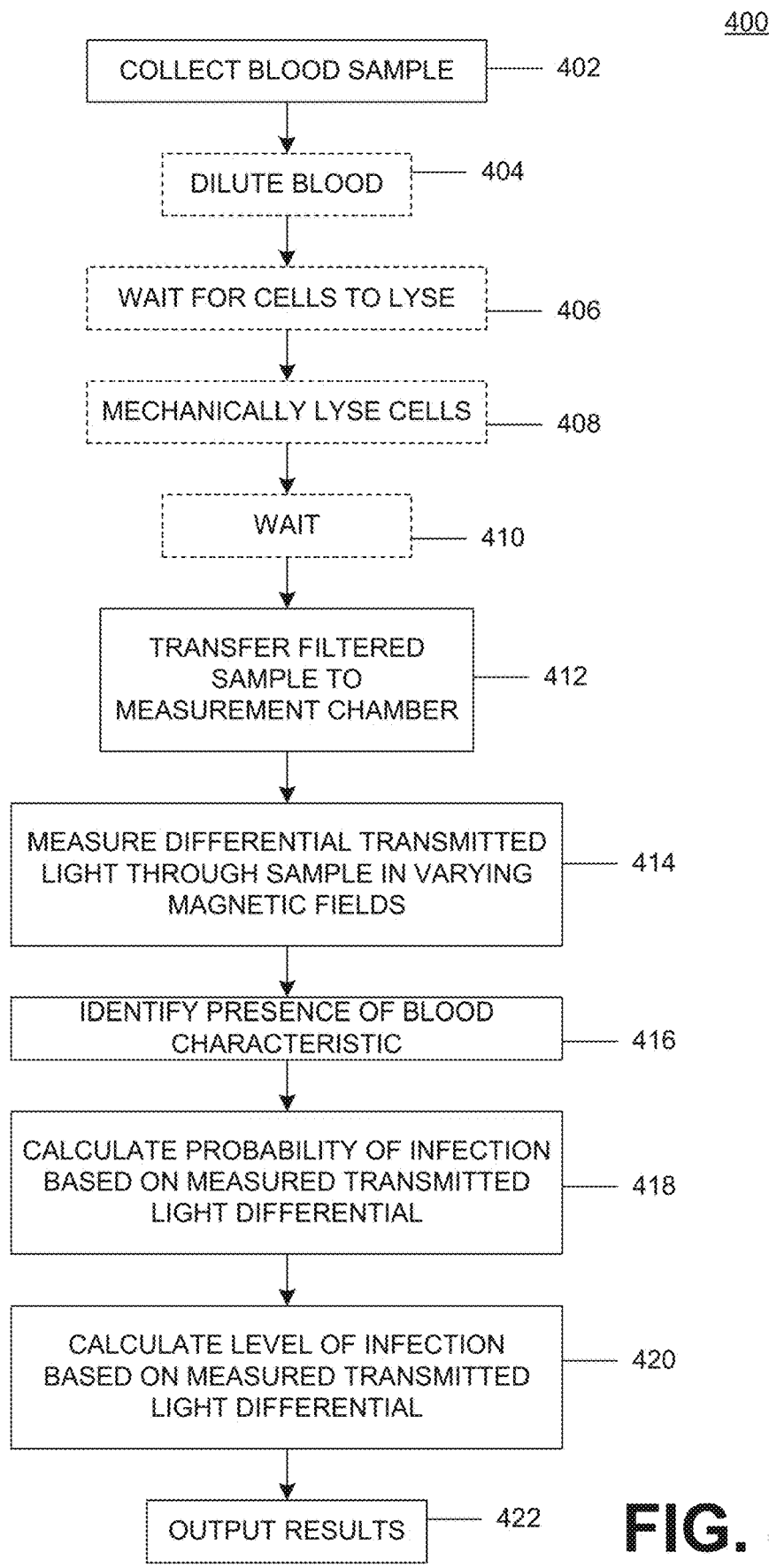
FIG. 4 illustrates an example disease and/or condition analysis method using the example magneto-optical detection system shown in FIGS. 3A-3B.

FIG. 4 is an example analysis method 400 using an MOD system, such as the one shown in FIGS. 3A-3B. The analysis of a patient sample, which is patient blood in this example, is performed to determine a blood characteristic, which can include the presence of a disease or condition, quantification of a disease or condition, likelihood of the presence of a disease or condition, a characteristic that can be indicative of a disease or condition, a quantification of a characteristic that can be indicative of a disease or condition, and/or other blood characteristic that can be effected by the presence of a disease or condition of the patient. The example method of FIG. 4 is performed using a reader and cartridge system, such as the example shown in FIG. 1, and the MOD system is included within the reader which can include additional systems and/or elements to analyze, quantify, identify and/or otherwise determine characteristics of a patient sample that can be indicative of the presence of a disease and/or condition of the patient.

An initial step 402 of the method 400 can include the collection of a patient sample for analysis, in this example, a blood sample. Alternative and/or further patient samples, such as saliva, tissue and/or other bodily fluids can be collected for analysis by one or more systems of the reader.

The collected blood sample 402 can then be prepared, if necessary or desired, for analysis. The preparation of the blood sample can include diluting the blood 404, which can be done by mixing the collected blood sample with a dilutant, such as deionized water or other fluid that dilutes the blood sample. The dilutant can alter the viscosity of the blood sample, the opacity or translucence of the blood sample, or otherwise prepare the blood sample for analysis using the reader. Preferably, the dilutant does not impact the resulting analysis of the blood sample and/or assists with preparing the blood sample for analysis. This can include lysing the cells of the blood sample to release the various cellular components for analysis, such as detection and/or quantification, by the reader. Lysing agents can include fluids, such as water or various chemicals, and powders.

Cellular lysing can take time, so a requisite amount of time may be required 406 to ensure adequate cellular lysing has occurred within the blood sample in preparation for analysis. The lysing of the cells of the blood sample can occur naturally, as part of a cellular death or destruction cycle, or can be enhanced or performed using chemical and/or mechanical lysing techniques 408. As previously discussed, adequate time can be waited 410, such as 5 minutes for lysing in water and 15 seconds for mechanical lysing using sonication, to achieve adequate lysing of the cells of the blood sample in preparation for analysis of the sample using the reader.

The blood sample can then be filtered before being transferred into a measurement chamber 412 of the cartridge. Filtering the sample can remove one or more components of the sample, such as debris from cell lysing, clots or agglomerations of cells, and/or other components that could affect the analysis or are otherwise undesirable or unneeded in the sample to be analyzed. An alternative approach is to filter, so the hemozoin for example, are one of the components left. The filter can be an element having structural features, such as pore size, or chemical features that allow the filter to restrain, remove, attract, or otherwise filter a particular component from the patient sample. An example filter can have a pore size of 1-5 microns to filter a blood-type or other patient sample. The patient sample or blood can be passed passively, by Brownian motion, or actively, by a pressure differential, through or across a fixed filter to remove the particular component. Alternatively, the filter can move through, about or be placed in the patient or blood sample to filter a component(s) from the sample.

A further preparation of the patient blood sample can include cleaning and/or concentrating the patient sample prior to analysis. Cleaning and/or concentrating the patient sample can include removing unwanted components of the patient blood sample prior to analysis. The various unwanted components are typically dispersed throughout the patient's blood and can interfere with an accurate reading of the patient sample. For example, the unwanted components can add noise to the detected data signal, can move in and out of the light transmission path that is transmitted through the sample, or and/or can otherwise obstruct the analysis of the patient sample.

An example cleaning and/or concentrating the patient sample can include appropriately diluting the patient sample anywhere between 100:1 to 2:1 or any other desired amount. The diluted sample lowers the effective concentration of the compound(s) being studied. The sample is then lysed, such as by sonication. The lysed patient sample is then centrifuged to separate one or more desired components of the patient sample from the remaining portion of the patient sample. The remaining portion of the patient sample, the supernate of the centrifuged sample, can be disposed of so that the one or more desired components of the patient sample remain. During centrifuging, hemozoin forms small pellets while some other blood components remain in suspension to form the supernate. The concentrated portion, in this specific example the hemozoin, is then diluted to a desired end volume. The re-diluted hemozoin is sonicated to loosen the hemozoin from the walls of the centrifuge chamber where it tends to adhere during centrifugation. Analysis of the cleaned and/or concentrated sample can then be performed using one or more systems of the reader.

Another example of cleaning and/or concentrating the patient sample prior to analysis can include passing the lysed diluted patient sample over a magnetic surface, such as a column of ferrite balls in a magnetic field. The magnetized ferrite surface attracts the magnetic components of the patient sample, while the remainder of the sample passes through which concentrates the magnetic component(s) of the patient sample and separating, or cleaning, the magnetic component(s) from the remainder of the patient sample. The magnetic component(s) of the patient sample can then be washed from the ferrite surface after removing the magnetic field. The sample can then be diluted, which can also be performed by the washing of the magnetic components from the ferrite surface, to an appropriate and/or necessary volume for analysis. The ferrite surface can also be sonicated and/or vibrated to assist with removal and/or washing of the magnetic component of the patient sample from the ferrite surface.

In further embodiments, the measurement chamber can be a chamber within the reader, with the patient blood sample transferred to the measurement chamber of the reader from the cartridge. An interface of the reader and/or cartridge can transfer a portion of the patient or blood sample from the cartridge into the measurement chamber of the reader. The patient sample can be transferred from the cartridge to the reader using a pressure differential, such as negative pressure in the reader measurement chamber to draw the sample from the cartridge or positive pressure applied to the cartridge to push the patient sample from the cartridge into the reader measurement chamber. The sample can be transferred from the cartridge to the reader through the same opening as the patient sample was originally transferred into the cartridge or through another opening or conduit of the cartridge or the chamber of the cartridge within which the patient sample is contained. Alternatively, the reader can include a piercing element to pierce a portion of the cartridge to withdraw the patient sample, or a portion, from the cartridge.

Light is then transmitted or passed through the blood sample and measured in a varying magnetic field 414, such as the system of FIGS. 3A-3B. The application of a varying magnetic field to the blood sample can cause magnetic, or paramagnetic, components of the patient, or blood, sample to align with the polarity of the applied magnetic field. The alignment of the magnetic, or paramagnetic, components of the blood sample affects the transmission of light through the blood sample. As such, a differential of light transmittance through the blood sample can be established by transmitting light through the blood sample with the application of a magnetic field in a first state, such as a lower strength and/or intensity of magnetic field or the absence of a magnetic field, and then applying the same light, same intensity and wavelength, through the blood sample while the magnetic field is applied in a second state, such as a higher strength and/or intensity of magnetic field or the application of a magnetic field. The differential of the transmitted light through the blood sample in the two states can indicate the presence and amount of a paramagnetic compound(s) within the blood sample. The applied magnetic field can be from one or more permanent magnets or electromagnet(s) that can be energized. Either the blood sample or the magnets can be moveable and in some examples, either is moveable or both are moveable. The magnetic field applied to the blood sample can be attuned to preferentially affect a specific magnetic, or paramagnetic, component(s) of the patient or blood sample. The application and/or variance of the magnetic field can also affect and/or impact other portions and/or components of the patient or blood sample.

The measured light transmission differential can be used to identify the presence of a sample, or blood, characteristic 416 as indicated by a magnetic or paramagnetic component of the analyzed blood sample. The blood characteristic can include the release and/or breakdown of hemoglobin, or components and/or products thereof, which can be indicative of a disorder or disease.

Based on the measured light transmission differential, a probability of an infection can be determined 418. The probability of an infection or disease can be expressed as a numerical value and/or a subjective likelihood, such as a high or low probability, based on comparing the measured light transmission differential to a database of known correlated measured values and infection probabilities, an algorithm to correlate measured light transmission differential with infection probability, a statistical analysis of the measured light transmission differential to determine an infection probability, and/or repeated analysis of the sample to determine an infection probability based on the measured light transmission differential. Additional statistical techniques, algorithms and/or other analysis techniques can be applied using the measured light transmission differential to determine an infection probability based on the collected and analyzed blood sample.

In addition to calculating an infection probability, a level of infection can be determined based on the measured light transmission differential 420. As with the calculation of the probability of infection, various statistical techniques, algorithms, and/or other analysis techniques can be applied to determine a level of infection. Additionally, a database, remote or local to the reader, can be used in the calculation of the level of infection. The database can contain algorithms, historical data, correlations of infection level to measured light transmission differentials, and/or other data that can be used to calculate the level of infection. Additionally, the sample can be analyzed multiple times to confirm or generate additional data to be used for the calculation of the level of infection and/or the probability of infection.

Once the analysis of the blood sample is complete, the results can be output 422. The output of the results can include the identified blood characteristic(s), which can include a disease, condition and/or ailment, the calculated probability of infection, the calculated level of infection, the calculated level of the bio-marker being measured and/or other information relevant to and/or determined, calculated, and/or identified during the analysis of the blood sample. The output can be displayed or relayed to the user in a visual output, such as on a display, auditory, such as by a speaker, or other manner. This can include transmitting the output results to an external device, such as a computer, through a wired or wireless connection or communication protocol.

Figure 5:
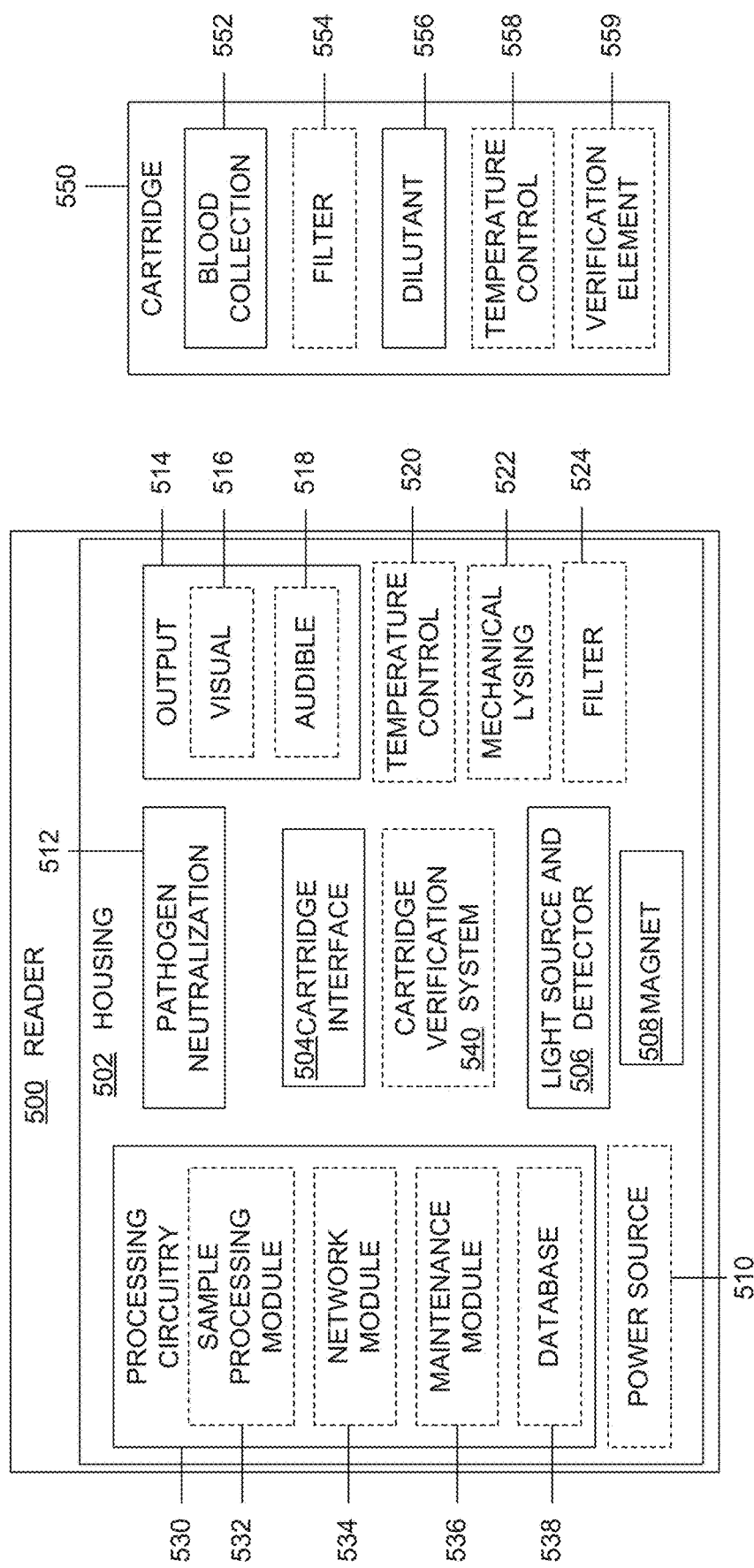
FIG. 5 is a block diagram of an example diagnostic system.

FIG. 5 illustrates an example reader 500 and a cartridge 550. The reader 500 can include all or a portion of the required systems and/or elements required to perform analysis of a patient sample. The cartridge 550 can include none or a portion of the systems and/or elements required to perform analysis of the patient sample. The reader 500 and cartridge 550 interface to perform the analysis, such as the method 400 of FIG. 4, of a patient sample.

The reader 500 includes a housing 502 that surrounds and encloses some portion or all of the reader components. FIG. 5 shows that the housing encloses all components of the reader 500, however, one of skill in the art will appreciate that any one or more components can be external to the housing, as needed or desired. As previously discussed, the housing 502 of the reader 500 is constructed of suitable materials in a suitably robust construction such that the reader 500 is rugged and portable. Example materials that can be included in the housing 502 include plastics, metals, and composites. The housing 502 can be constructed of multiple or a singular material and can include geometry and/or structural features that enhance the usability of the reader 500. Such features can include a smooth outer surface that is easily cleaned, grips or handles for carrying the reader 500, shock protection and/or increased structural strength in locations to prevent damage to the internal components of the reader 500, insulation to limit the transfer of heat through the housing 502 or shield magnetic fields sourced within the housing 502, a membrane or construction to prevent the intrusion of moisture and/or dust into the interior of the reader 502, connections, ports and/or interfaces for connecting the reader 500 to an external element and/or device using a physical or wireless connection, instructions regarding the use of the reader 500, identification markings such as a serial number and/or additional necessary or desirable features that can facilitate the safe, effective, efficient and/or proper use of the reader 500. The housing 502 can feature access points, such as removable or openable panels, to allow access to the interior of the reader 500 for maintenance and/or repair of the internal components, elements and/or systems of the reader 500. Additionally, the housing 502 of the reader 500 can be removable or separable from the other components, elements and/or systems of the reader 500, allowing the replacement of the housing 502, easing the cleaning of the housing 502, providing access to the components, elements and/or systems of the reader 500 and/or other abilities that require and/or made easier by the removal of the housing 502 of the reader 500.

The portability of the reader 500 can be an important consideration in the design and packaging of the reader 500, including the housing 502. The reader 500 may need to be rugged and easily transported so that it can be moved to and used in a variety of embodiments. Considerations, such as operating environment and access to infrastructure, can be considered when designing and/or constructing the reader 500 such that the reader can be used safely, effectively, and efficiently in a variety of environments and/or locations reliably. Depending on the environment of and infrastructure available in a particular location in which the system is to be used, the housing can be customized to best operate in that location by the addition and/or modification of existing reader features. Alternatively, the reader 500 can be designed and/or packaged to be more permanently located, such as in a laboratory, clinic, or other setting.

The housing 502 of the reader 500 includes a cartridge interface 504 that interacts with and/or engages the cartridge 550 for analysis of a patient sample. The cartridge interface 504 can be a slot that is shaped to receive the cartridge 550. The user inserts the cartridge 550 into the slot in preparation for analysis of the patient sample. The slot can include internal geometry that aligns and/or orients the inserted cartridge 550 in a proper alignment and/or orientation for the components, elements and/or systems of the reader 500 to perform the requisite or desired analysis of the patient sample contained within the cartridge 500. For example, the cartridge interface 504 can accept a variety of cartridges 550 having different cross-sections, such as square, rectangular, and circular cross-sections. The unique shape of each cartridge 550, the unique cross-section, can interact with the geometry of the cartridge interface 504 to properly align the cartridge 550 within the reader 500 for analysis. For example, the circular cross-section cartridge can insert into the cartridge interface 504 to a first position at a first orientation, the square cross-section cartridge can insert into the cartridge interface 504 to a second position at a second orientation. The various orientations and positions a specific cartridge 550 can be inserted into the cartridge interface 504 can be the same or different for multiple disease-specific cartridges 550.

The reader 500 can also include a cartridge verification system 540. The cartridge verification system 540 can be integrated with or separate from the cartridge interface 504 and/or included internal to or external from the reader 500. The cartridge verification system 540 can verify the legitimacy of a cartridge to assist with efficient and effective analysis of a patient sample. An example verification system 540 can include a verification element 559 of the cartridge 550 that interacts with the cartridge verification system 540 to verify the cartridge prior to further processing of the patient sample. Once the cartridge is verified, further analysis of a patient sample contained within the cartridge can be allowed to proceed. The verification of the cartridge can be the threshold analysis of the in vitro diagnostics process of the patient sample, in some examples. This verification can include limiting the analysis to a specific single or multiple analyses based on the cartridge verification.

A positive engagement or lock in the reader 500 can engage the cartridge 550 when properly and fully inserted. This engagement can also provide a tactile, audible, and/or visual cue to the user to signify proper insertion or interfacing of the cartridge 550 and reader 500. An example positive engagement or lock can include a notch and protrusion arrangement, the notch is sized to receive and releasably restrain the protrusion when engaged such that the notch of one element, the reader 500 or cartridge 550, engages the protrusion on the opposite element, reader 500 or cartridge 550, to releasably connect, interface with and/or engage the two elements, the reader 500 and cartridge 550, together. When prompted, such as when the analysis is completed or an error situation, the user can remove the cartridge 550 from the reader 500.

The cartridge interface 504 can also include an actuator or other element of the reader 500 that assists with the proper insertion and/or interfacing of the cartridge 550 and reader 500. The actuator can engage the cartridge 550 before the cartridge is fully inserted, the actuator can then position the cartridge 550 in a proper alignment and/or orientation with the reader 500 for the reader 500 to analyze the patient sample within the cartridge 550. When prompted, such as automatically by the reader 500 or manually by the user, the actuator can "eject" or disengage the cartridge 550 from the reader 500. The disengagement can fully or partially remove the cartridge 550 from the reader 500. Alternatively, the actuator can assist with the engagement or interfacing of the cartridge 550 with the reader 500 and not with the disengagement of the cartridge 550 and reader 500. In this example, the user can be required to remove the cartridge 550 from the reader 500 when prompted.

The cartridge interface 504 can be shaped to engage one or more specific cartridges 550, which prevents the insertion of an incorrect or improper cartridge 550 within the reader 500. The cartridge interface 504 can also be reconfigurable, either manually by a user or automatically by the reader 500 to accommodate a specific cartridge design to perform one or more specific analyses of a patient sample. For example, a user can input a desired or required analysis to be performed on a patient sample, the reader 500 can then reconfigure or prompt the reconfiguration of the cartridge interface 504 to accept a specific cartridge 550 that corresponds to the requested analysis.

For example, the cartridge interface 504 can include multiple configurable elements, such as panels, that can be configured and/or arranged automatically in response to a received analysis to be performed, such as a user-selected infection or disease for which to analyze the patient sample. The now configured and/or arranged configurable elements of the cartridge interface 504 are in a specific geometry into which only a compatible cartridge can be inserted. The analysis to be performed can be an input by a user into the reader 500 or from a remote administrator or system. In a further example, a specific cartridge interface 504 can include removable and/or replaceable cartridge interfaces 504 that can be removed from and/or inserted in the reader 500. Each cartridge interface can include geometry to accept a specific cartridge design(s). Additionally, the inserted cartridge interface 504 can be detected or otherwise communicated to the reader 500 and the reader 500 can limit available options, such as the analyses that can be performed, based on the inserted cartridge interface 504. Each cartridge interface 504, or cartridge interface 504 design or geometry, can correspond to a specific analysis or analyses. Further, the reader 500 can be limited to the specific analysis or analyses corresponding to the particular cartridge interface 504 and/or cartridge interface 504 geometry.

In a further example, the cartridge interface 504 can initially accept any inserted cartridge. Once a cartridge is inserted, the cartridge interface 504, a sensor or other reader 500 system or element can detect the cartridge type and the corresponding analysis or analyses that can be performed based on the cartridge type. The cartridge interface 504 can manipulate the cartridge position and/or orientation, the reader 500 can properly position and/or orient analysis systems or elements relative to the cartridge, and/or the cartridge interface 504 and/or reader 500 systems or elements can be configured to perform the analysis or analyses corresponding to the cartridge type.

Also, a sample processing module 532 of the processing circuitry 530 of the reader 500, or an external sample processing system and/or element, can alter the processing of the sample analysis data to correct, compensate or otherwise modify the collected sample analysis data based on the type of cartridge inserted within the reader 500. Instead of or in addition to positioning and/or aligning the cartridge and/or reader 500 analysis systems relative to the reader, the processing of the collected sample analysis data can be manipulated and/or modified to compensate based on the type of cartridge inserted. Additional modifiers can include compensating for position/alignment errors caused by improper alignment/positioning of the cartridge relative to the analysis systems and/or elements.

Further, the cartridge interface 504 can include multiple orientation and/or alignment features that engage specific cartridge 550 features to properly align a specific, inserted cartridge with a specific analysis process. For example, a first cartridge for a first specific analysis is inserted into the cartridge interface 504 which guides, aligns, and/or orients the first cartridge properly in a first position for the first analysis to be performed, a second cartridge for a second specific analysis can be interested in the same cartridge interface 504, which can properly guide, align, and/or orient the second cartridge in a second position for the second analysis to be performed. In this manner, the cartridge interface 504 ensures the proper positioning of a variety of specific cartridge designs within the reader 500 allowing a corresponding variety of specific analyses to be performed, each analysis corresponding to one or more specific cartridge designs.

The cartridge interface 504 can also include a number for position points corresponding to various steps of analysis. For example, an analysis can require that the cartridge 550 is inserted partially to a first position within the reader 500 to perform a first step of the analysis, the reader 500 can prompt the user to advance or move the cartridge 550 to a second position, such as further insertion of the cartridge 550 within the reader 500, to perform a further step of the analysis. Each position can include a tactile, audible, or visual indication to a user manually inserting the cartridge 550 within the cartridge interface 504 to assist the user with properly position the cartridge 550 within the cartridge interface 504. An actuator, such as described previously, can position the cartridge 550 at the various analysis require positions automatically, or can assist the user with the cartridge 550 positioning.

Insertion of the cartridge 550 into cartridge interface 504 of the reader 500 can automatically initiate or prompt a user to initiate analysis of the patient sample contained within the cartridge 550. An actuator and/or sensor can be connected to the processing circuitry of the reader 500 and triggered by and/or sense the insertion of the cartridge 550 to automatically initiate or to prompt a user to initiate the analysis of the patient sample. Initiating analysis of the patient sample can include powering-up, preparing, and/or running the various analyses systems and/or devices, such as a light source and detector 506 or mechanical lysing 522. In some examples, the user need only insert the cartridge 550 in the reader 500 to actuate or trigger the entire diagnostics process to an output.

The cartridge interface 504 and additional elements, such as guides or actuators can be integrated into the housing 502 of the reader 500 or can be separate components, elements and/or systems. Each of the additional elements can be further separable from each other allowing for replacement, substitution, repair and/or maintenance of the additional elements as necessary or required.

The reader 500 can include a single cartridge interface 504, such as the example shown in FIG. 1, or can include multiple cartridge interfaces 504 in the same reader 500. The multiple cartridge interfaces 504 can allow the reader 500 to analyze multiple patient samples simultaneously and/or in succession by allowing more than one cartridge 550 to be interfaced with the reader 500. Additionally, each of the multiple cartridge interfaces 504 can accept the same and/or different cartridges to perform the same and/or different analyses. Further, in conjunction with a multi- or singular cartridge interface 504, a guide, rack, carousel and/or system can hold multiple cartridges in preparation for analysis. The guide, rack, carousel and/or system can feed or guide, actively or passively, cartridges 550 to the reader 500 by the cartridge interface 504 allowing multiple patient samples and/or cartridges 550 to be analyzed with minimal interruption between the analyses.

The reader 500 shown in FIG. 5 includes a light source and detector 506. The light source and detector 506 can be part of an MOD, the optical portion, or other analysis and/or detection system within the reader 500, to be used in performing analysis of patient samples. The light source emits light and the light detector receives light, signals, or outputs from the light detector. The detected light can be used to quantify and/or characterize the light received by the light detector. In example embodiments, the light source and detector can be arranged opposite one another, separated by a distance along a single axis. In this example, the light detector can receive light emitted from the light source across the distance, which can include an intervening object such as a patient sample. In this example, the laser and detector are positioned on opposing sides across the patient sample contained in the cartridge and the cartridge has an optical window(s) that allow for complete transmission of the laser light through the patient sample. The laser light transmission path through the patient sample can be entirely through the fluid, below any free surface of the fluid if the sample chamber is not completely full of the patient sample. Alternatively, the light source and light detector can be arranged offset from one another allowing the light detector to quantify and/or characterize light reflected or refracted by an object, such as a patient sample. Further, multiple light sources and/or light detectors can be included in the reader 500.

The positioning and structure of the cartridge 550 within the reader 500 can be such that the light source and light detector are positioned relative to the inserted cartridge 550 to ensure that the light transmission path between the light source and light detector passes entirely through the fluid patient sample within the cartridge 550 below any free surface of the patient sample that might exist in the cartridge. The light source can emit a consistent and steady light, which can be further standardized by collimating and/or polarizing the emitted light that is transmitted through the patient sample and received by the light detector. As light is transmitted through the patient sample, components within the patient sample can absorb, scatter, reflect or otherwise affect the incoming light. The light detector therefore registers an altered quantity and/or characteristic of the light transmitted through the patient sample than light transmitted directly from the light source to the light detector with no intervening patient sample. The altered quantity and/or characteristic of light transmitted through the patient sample can be included and/or used during analysis of the patient sample. Optionally, the emitted light from the light source can be divided, such as by a beam splitter. A first portion of the split beam can be passed through the sample to a first light detector and a second portion of the split beam can be directed to a second light detector with no intervening sample. The transmitted light differential can be measured based on the registered transmittance by the first and second light detectors.

The light source can be several different light emitting sources, such as an incandescent bulb, a fluorescent bulb, a light emitting diode (LED), a laser, the sun or other light source. In some example embodiments, the light source can emit a steady light having known characteristics or properties. Alternatively, the light source can emit varied light, such as light emitted by an incandescent bulb. The light source can be modulated to change the intensity and/or wavelength(s) of transmitted light. Such light can be standardized, entirely or in portion, using filters and/or lenses through which the emitted light is transmitted. For certain analyses, the variance in emitted light properties may not affect the analyses performed, which can be due to the short duration of the analysis and/or other features of the analysis. An example light source can emit light directly, or with the use of filters and/or lenses, emit light with a wavelength of approximately 650+ nanometers.

The light detector receives light emitted from the light source and then transmitted, refracted and/or reflected through/from the patient sample. The output from the light detector can be used to quantify and/or characterize the light received by the detector. Alternatively, the light detector can quantify and/or characterize the received light itself and output or transmit data or a signal indicative of the quantified/characterized received light. Example light detectors can include photodiodes, digital imaging elements such as a charge coupled device (CCD), a CMOS imager, a photovoltaic array, and/or other suitable sensors or detectors capable of registering a change in response to received light.

The light source and light detector 506 can be connected to processing circuitry 530 of the reader 500. The processing circuitry 530 can trigger the emission and potentially control the characteristics of light from the light source and/or receive signals from the light detector based on the quantity and/or characteristics of light received by the light detector.

Reflective surface(s) can be positioned within the housing 502 and/or positioned relative to the patient sample such that the light emitted from the light source is transmitted multiple times through the patient sample before being received by the light detector. Each of the multiple transmission paths within the patient sample can occur below a free surface of the sample so the entirety of the multiple light transmission path through the sample occurs within the fluid sample. The geometry of the cartridge can assist to ensure that the laser transmission does not extend above any existing free surface of the patient sample.

The repeated transmission of light through the patient sample assists with the analysis of the patient sample. The repeated transmission of the light through the sample increases the transmission path of the light which can correspondingly increase the sensitivity, reliability and/or accuracy of the detected light transmission since the light is transmitted through a larger portion or volume of patient sample and has a higher probability of contacting an element or component within the sample that can result in a change in a property and/or characteristic in the light transmitted through the patient sample.

The reader 500 can include a magnet 508. The magnet can be included as a portion or part of an MOD, such as the MOD example shown in FIGS. 3A-3B, or used in analysis of a patient sample. The magnet 508 can be movable within the reader 500, allowing the magnet to be moved relative to the patient sample. This can subject the patient sample to the presence of a magnetic field and/or the presence of a varying magnetic field as the magnet 508 is moved relative to the patient sample. Alternatively, the patient sample can be moved relative to the magnet 508. The magnet 508 can be a permanent magnet and can include a single magnet or multiple magnets. In an example, the magnet includes two permanent magnets, such as the MOD examples taught by U.S. Ser. No. 14/766,523, which is incorporated herein by reference in its entirety. An example MOD includes two permanent magnets that are positioned on opposite sides of a patient sample, which can also be on opposites sides of a cartridge containing a patient sample. The magnet can also be an electromagnet(s) that can be energized as required or desired during analysis of the patient sample. Further, the strength and polarity of the electromagnet can be varied or set to a required or desired level and/or orientation.

The reader 500 can include an internal power source 510 that supplies the necessary power to run the components, elements and/or systems of the reader 500 to perform analysis of patient samples and/or preserve a minimal, required functionality of the reader. The power source 510 can supply power to the processing circuitry 530, the light source and light detector 506, the magnet 508 and/or other component, elements and/or systems of the reader 500. The power source 510 can include one or more batteries or other energy storage devices that provide a required or desired level of power for the reader 500. Additionally, the power source 510 or a portion thereof can be external to the reader 500 and connected thereto as needed or required. External power sources can include batteries or other energy storage devices and/or a connection to a nearby power source such as a generator, municipal power, or solar array.

The reader 500 can also include pathogen neutralization 512. The pathogen neutralization 512 can include physical components, such as a device or system, and/or a chemical component. There are many different methods of pathogen neutralization and many different devices/systems capable of performing the methods. The goal of pathogen neutralization is to target specific undesirable biological material, such as diseases and parasites, for destruction/neutralization or to destroy biological material indiscriminately, such as by sterilization. Various systems, such as devices or chemicals that interrupt biological processes and/or cause the breakdown of biological materials can be to neutralize pathogens within a reader 500 and/or a cartridge 550.

An ultraviolet (UV) light source is an example pathogen neutralization 512 device that could be used within the reader 500 is e. Exposure to UV light has a debilitating effect on biological material and exposure to intense UV light can cause biological destruction. A UV light source can be placed within the reader 500 and activated to bathe the interior of the reader in UV light, which neutralizes at least a portion of the biological material, including pathogens, within the reader 500. Alternatively, the UV light can be continuously powered on when the reader 500 is in use. The UV light can also be targeted, with one or more UV light sources placed in specific areas of the reader 500 to perform the desired pathogen neutralization. Additionally, the UV light can be positioned to penetrate and/or bathe a cartridge 550 inserted within the reader 500 to neutralize the patient sample within the cartridge 550 after analysis has been performed. A timing device can be connected to the UV light source to ensure that the UV light source is activated for a necessary amount of time to perform the pathogen neutralization. A photo- or light detector can also be included, such as the light detector of the light source and light detector 506, that can monitor the output of the UV light source to check the continued efficacy of the UV light source and/or monitor the output of the UV light source to ensure it is activated for a long enough duration to achieve a level of pathogen neutralization. The emitted UV light can affect materials, such as plastic, adversely causing them to become brittle. In some examples, shielding can be included within the housing 502 of the reader 500 to protect areas, components, elements and/or systems which could be damaged by UV light exposure.

A further pathogen neutralization 512 system can include the use of chemicals to neutralize biological material within the reader 500 and/or cartridge 550. A chemical based pathogen neutralization 512 system can include the application of chemicals within the reader 500 on a temporary or permanent basis. That is, a chemical application can be applied within the reader 500 during manufacture, the applied chemical application can continuously destroy at least a portion of biological material that contacts a surface upon which the chemical was applied. A temporary chemical based pathogen neutralization 512 system can include a chemical dispersal system that deploys or applies chemicals within the reader 500 and/or cartridge 550 on actuation, the chemicals contact various surfaces, elements, components and/or systems of the reader 500, destroying at least a portion of biological material thereon.

In an example embodiment, pathogen neutralizing chemicals, such as a bleach-based solution, can be sprayed, fogged, and/or distributed about the interior of the reader 500 to perform the pathogen neutralization. The pathogen neutralizing chemicals can be added to the reader 500 by a user, contained within a vessel that is housed, inserted within or fluidically connected to the reader 500. The pathogen neutralizing chemicals, such as the bleach-based solution, can be prepared as needed or can be prepared and stored for later use. An indicator or timer can be included that can indicate to a user once the pathogen neutralization process is complete. The indicator or timer can also prevent the use of the reader 500 until the pathogen neutralization process is complete. As with the previously described pathogen neutralization systems, the chemical-based pathogen neutralization method can also neutralize at least a portion of biological material on and/or within a cartridge 550 inserted within the reader 500. Additionally, the chemical-based pathogen neutralization chemicals can be pumped or transported through the various components, elements and/or systems of the reader 500, to disinfect portions that can contact a patient sample, which helps to prevent cross-contamination of patient samples.

An example pathogen neutralization system to neutralize at least a portion of the pathogens of the cartridge 550 can include a portion that is included in the cartridge 550. Pathogen neutralization material, such as powders, fluids and/or other components can be included in the reader 500 and/or cartridge 550 assist with neutralization of pathogens within the cartridge 550. The pathogen neutralization material can be included in a portion of the cartridge 550 and dispersed into the collected sample and/or other portions of the cartridge 550 upon actuation, such as by a user, the reader 500, the cartridge 550, or another source. The pathogen neutralization material can also be integrated with a portion of the cartridge, such as included in the dilutant 556. Alternatively, the pathogen neutralization material can be included in the reader 500 and the reader 500 can circulate, or otherwise insert, the pathogen neutralization material into the cartridge 550. The pathogen neutralization material can be targeted to a specific pathogen or be a general wide spectrum pathogen neutralizer.

The reader 500 can include an output 514 that includes one or more visual 516 and/or audible 518 outputs although in other examples the output is data and does not include visual and/or audible outputs. The output 514 shown in FIG. 5 communicates information regarding the status of the reader 500, the results of analysis of a patient sample, instructions regarding use of the reader 500 and/or other information to a user or other computing device. The visual 516 output 514 can include a display, such as a screen, such as a touchscreen, lights, and/or other visual indicators. The touchscreen used to display information, such as analysis results, to the user can also be used by a user to input to the reader 500. The audible 518 output 514 can include a speaker, buzzer, or other audible indicators. The output 514, visual 516 and/or audible 518, can be output through an external device, such as a computer, speaker, or mobile device connected physically and/or wirelessly to the reader 500. The output 514 can output data, including the collected analysis data and/or interpretative data indicative of the presence or absence of an infection, disease and/or condition within the patient and/or the patient sample. An example can include the presence of hemozoin within the patient sample. The interpretive data output can be based on the analysis data collected and processed by the processing circuitry 530 of the reader 500.

The reader 500 can also include temperature control 520. The temperature control 520 can actively and/or passively control the temperature of at least a portion of the reader 500. Active temperature control 520 can include heating and/or cooling a portion of the reader 500. Temperature control 520 can also include heating one portion of the reader 500 and cooling another portion of the reader 500. The temperature control 520 can include a refrigeration system, resistive heater, infrared heater, thermoelectric elements, radiator, and/or other temperature control devices and/or systems. One example is thermoelectric control of the temperature of the light source which in one example is a laser diode. Passive temperature control can include structures to contain a thermal material in portions of the reader 500. This can include holders for ice, hot water, ice packs, and other thermal materials, the holders retain the thermal material in portions of or about components, elements and/or systems of the reader 500.

The reader 500 can also include mechanical lysing 522. Mechanical lysing 522 can assist with the lysing of cells of a patient blood sample within a cartridge 550 or the lysing of the patient blood sample within the reader 500. Mechanical lysing 522 can include a physical disruptor, or portion thereof, an agitator, a sonicator that can apply sound energy to the patient sample, and/or other mechanical lysing device or system. The mechanical lysing 522 can interface with and/or engage the cartridge 550 to facilitate the lysing of the patient sample. The mechanical lysing 522 can be mechanically powered, such as by a wound spring, or electrically powered, such as by a reader 500 power source 510.

The reader 500 can also include a filter 524. The filter 524 can attract, extract, collect and/or otherwise remove unwanted components or particles in a patient sample of the cartridge 550 or concentrate the wanted components or particles. The filtering of the patient sample by the filter 524 can occur as the patient sample is transferred from the cartridge 550 into the reader 500 or the patient sample can be transferred from the cartridge 550, through the filter 524 and back into the cartridge 550 for analysis. The filter 524 can include structural and chemical features that allow the filter 524 to remove desired or required components from the patient sample. The filter can be affixed in a stationary position to contact the patient sample or moveable through the patient sample to filter the patient sample.

Processing circuitry 530 can be included in the reader 500 to receive input from various components, elements and/or systems, such as the light source and light detector 506, of the reader 500. The processing circuitry 530 can process the received inputs to perform analysis of the patient sample and output results and/or data of that analysis. The processing circuitry 530 can include a sample processing module 532, a network module 534, a maintenance module 536 and a database 538. The various elements, 532, 534, 536, 538 and others, of the processing circuitry 530 can be removable and/or replaceable, allowing replacement and addition of various elements to the processing circuitry 530. In example embodiments, all or a portion of the processing circuitry 530 can be included in the reader 500 and a portion of processing circuitry included in the cartridge 550. The processing circuitry 530 can also control the various components, elements and/or systems, such as pathogen neutralization 512, mechanical lysing 522, the light source, and others, of the reader 500.

The processing circuitry 530 can initiate and/or control the analysis of a patient sample within a cartridge 550. The processing circuitry 530 can include preset routines that can be executed by the reader 500 to analyze a patient sample. The preset routines can include prompts for user input and/or the processing circuitry 530 can prompt a user for input before, during and/or after analysis of a patient sample. User prompts can include acknowledgement and/or authorization to proceed through one or more portions of the analysis process. Alternatively, the processing circuitry 530 can initiate, perform, and/or direct the analysis of the patient sample automatically without user prompts. The processing circuitry 530 can proceed through the various processes and procedures of an analysis of a patient sample, engaging any one or more of the reader 500 systems and collecting the analysis data. The processing circuitry 530 can further automatically process the collected data and transmit a result to a user or other, including an indication the analysis is complete, information regarding the analysis and/or other indications. The processing circuitry 530 can also transmit the collected data to an external system or device for processing and can transmit a result to the user and/or the result can be transmitted by one or more of an external system and/or device.

The sample processing module 532 can receive inputs from the light detector of the light source and light detector 506. Based on the received light detector data, including varying magnetic fields, the sample processing module 532 can determine at least a characteristic of the patient sample, such as a disease or condition, a probability of a characteristic, such as an infection, of the patient sample and quantification of a characteristic, such as a parasite level, of the patient sample. The sample processing module 532 can output an indication of a characteristic, such as an infection, and/or other various data based on the analysis of the patient sample. The output from the sample processing module 532 can be output through the output 514 of the reader 500 or transmitted to an external device and/or system, such as a computer, mobile device, and remote server or database.

The sample processing module 532 can analyze the patient sample to determine a hemoglobin characteristic, such as a hemoglobin affecting disease and/or condition, based on the data from various components, elements and/or systems of the reader 500. The results of the analysis can be output from the sample processing module 532 to the output 514 to convey the information to a user or other.

A network module 534 can be included in the processing circuitry 530. The network module can allow the reader 500 to communicate with other readers, computing devices, servers, databases and/or other devices or systems. The network module 534 can communicate with another device through a physical, such as a local area network (LAN), Universal Serial Bus (USB), and/or wireless, such as Bluetooth®, connection. In an example, the reader 500 can communicate to a remote server through the network module 530 allowing the reader to upload patient sample analysis to the patient's medical records stored on the remote server. The network module 534 can transmit and/or receive communication to/from the reader 500 and another device or system. In another example, information on the patient can be downloaded to the reader and added to the display or output or used in the analysis(es). For example, demographic information such as age, sex, etc.

A maintenance module 536 can be included in the processing circuitry 530. The maintenance module 536 can perform, initiate and/or prompt maintenance, calibration, and/or other processes of the reader 500. Maintenance of the reader 500 can include prompting a user to clean a portion of the reader 500, to replenish resources of the reader 500 and other regular or unscheduled maintenance of the reader 500. Calibration of the reader 500 can include testing components, elements and/or systems of the reader 500 to check if the reader 500 is in an effective operable state. Additionally, the calibration of the reader 500 can be performed by the maintenance module 536 and/or prompt a user to perform necessary calibration procedures to allow the reader 500 to perform patient sample analysis effectively and correctly. The maintenance module could also allow automated or semi-automated ordering of supplies or service.

A database 538 can be included in the processing circuitry 530. The database can record patient sample analysis data, patient data, statistical data, test conditions, and other data. The network module 534 can communicate with the database 538 exporting and/or importing data. The database 538 can be stored on removable and/or permanent data storage within the reader 500. The database can also occur in whole or in part remote from the reader.

Statistical data of the database 538 can be used during analysis of a patient sample by the sample processing module 532 to assist and/or perform the analysis of a patient sample. This can include tables with reference light transmission amounts and/or characteristics through various patient samples having determined infections, diseases and/or conditions and levels of these infections, diseases and/or conditions. Additionally, the database 538 can include statistical analysis techniques and/or algorithms that can be used by the sample processing module 532 to determine, calculate or otherwise analyze the patient sample.

The database 538 can also include specific information, such as prior patient analysis results. Such results can be used to determine if the detected condition is new and/or an existing condition. Additionally, the severity of the condition, such as an infection, can be tracked for a particular patient to assess their treatment progress.

The cartridge 550 can contain the patient sample for analysis. The cartridge 550 can be inserted in the cartridge interface 504 and the patient sample analyzed or transferred to the reader 500 for analysis by the components, elements and/or systems of the reader 500. The cartridge 550 can include a blood collection device or system 552, a filter 554, a dilutant 556, a temperature control device and/or system 558 and a verification element 559.

Blood collection 552 of the cartridge 550 can include a device and/or system for collecting, storing, and/or analyzing a patient's blood sample, which can include a passive or active blood collection device or system, a blood sample storage chamber, a blood sample analysis chamber and/or other chambers, devices and/or systems to assist or facilitate the collection of a blood sample and analysis of the blood sample.

Active blood sample collection can include the use of a needle, capillary tube or pipette. In an example embodiment, the cartridge 550 can include a needle that can be actuated to deploy from the cartridge 550, piercing a patient's skin and extracting a sample that is drawn into the cartridge 550 and stored for analysis. A further active blood sample collection 552 can be a pipette-like system. The user or other can apply pressure to a bulb or deformable portion of the cartridge 550, the release of pressure on the bulb or deformable portion can draw at least a portion of a patient blood sample into the cartridge 550. The patient can be lanced, poked or pierced to cause bleeding, the blood can be sampled to draw at least a portion of the blood into the cartridge 550 for analysis.

The blood collection 552 can include a lancet or a piercing instrument that can pierce skin to cause bleeding. The blood can be collected using the cartridge 550 to obtain the patient blood sample. Collection of the blood sample can include retraction of the lancet or piercing instrument, carrying a portion go the patient blood into the cartridge 550 for analysis. The blood collection 552 can also include a sealed chamber that is sealed and has negative pressure. A needle can pierce the patient and pierce the sealed chamber, the negative pressure of the sealed chamber causing blood to flow into the sealed chamber due to the pressure differential.

The blood collection 552 can also include a capillary tube that can passively collect a blood sample using capillary action. The patient is caused to bleed, such as by a lancet or other inducing technique, and the capillary tube is placed in the blood to draw a sample into the capillary tube of the cartridge 550 for analysis.

The cartridge 550 can include a filter to filter the patient sample within the cartridge 550. The filter can be placed to filter the patient sample as it is drawn into the cartridge 550 through, before and/or after the blood collection 552. In another example, the filter 552 can filter the sample after it has been stored in the cartridge 550. As previously described, the filter can include structural and/or chemical features to filter a patient sample as necessary or desired.

Dilutant 556 to dilute, treat and/or prepare the patient sample for analysis can be included in the cartridge 550 to be mixed with the collected patient sample. The dilutant 556 can be stored in a dilutant chamber within the cartridge 550 and separate from the patient sample and mixed automatically or manually. The dilutant 556 can be pre-loaded in the same chamber, a mixing chamber or patient sample chamber, that the patient sample will be stored within the cartridge 550. Alternatively, the dilutant 556 can be stored in the cartridge 550 remote from the patient sample storage and mixed with the patient sample. The dispensing of the dilutant 556 into the patient sample can be triggered manually by the user, or automatically, such as by the cartridge 550 or reader 500. Alternatively, or additionally, the dilutant used to prepare the patient sample for analysis can be stored within the reader 500. The reader 500 can add the dilutant to the patient sample within the cartridge 550 or can be added to a sample, or mixing, chamber of the reader 500 into which the patient sample, or portion thereof, from the cartridge 550 is transferred. As with the cartridge 550, the sample, or mixing chamber, of the reader 500 can also be pre-loaded with the dilutant.

The cartridge 550 can also include temperature control 558, which can include active and/or passive temperature control systems and/or methods. Passive temperature control 558 can include insulation, structural design features and/or chemical design features. The passive temperature control 558 can maintain the temperature of the cartridge 550 to preserve a collected patient sample. Active temperature control 558 can include electronic elements, such as thermoelectric elements that can heat or cool at least a portion of the cartridge 550, for example to regulate the temperature of the cartridge 550 or a portion thereof. Temperature control 558 can include heating and/or cooling the temperature of the cartridge before, during and/or after the collection of a patient sample and/or the analysis of the sample. The temperature control 558 interfaces with the reader 500 and/or an external device to regulate the temperature of the cartridge 550.

Figure 6:
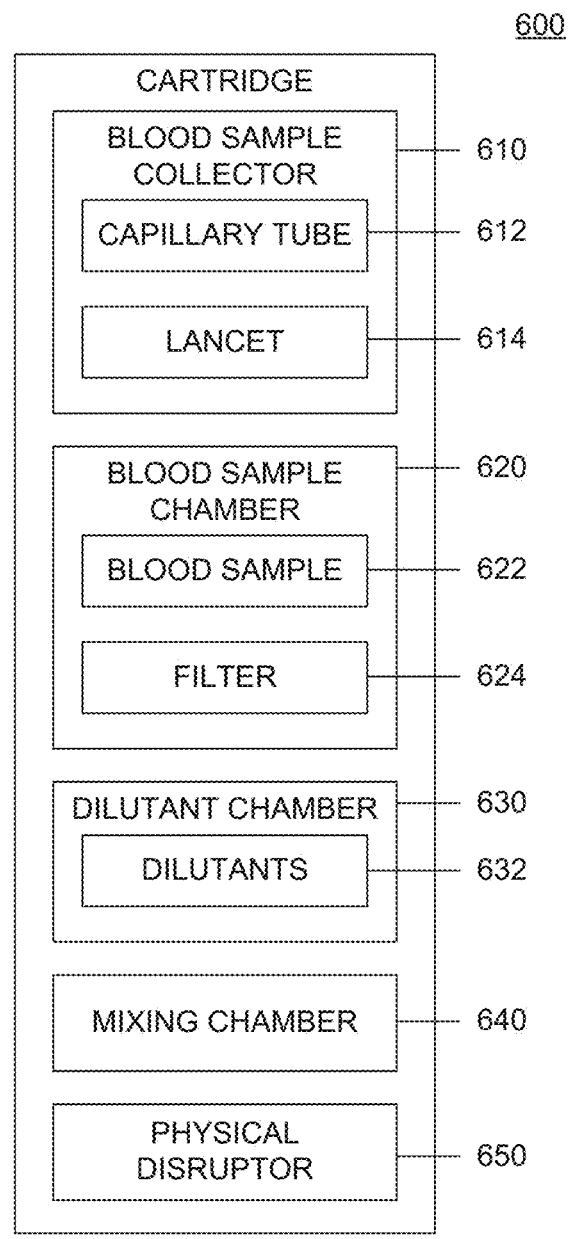
FIG. 6 is a block diagram another example cartridge.

FIG. 6 is a further example cartridge 600, which can include a blood sample collector 610, a blood sample chamber 620, a dilutant chamber 630, a mixing chamber 640 and/or a physical disruptor 650. The various components of the cartridge 600 can be arranged in various configurations depending on the analysis to be performed and/or other environmental and/or use considerations. In the example shown in FIG. 6, the cartridges 600 components can be interchangeable allowing a complete cartridge 600 to be assembled from various components.

The blood sample collector 610 of the cartridge 600 can collect a blood sample from a patient. The collector 610 can include devices, components and/or systems to assist or perform the collection of the blood sample from a patient. The blood sample collector 610 can include a capillary tube 612 and/or a lancet 614. The capillary tube 612 can use capillary action to draw a blood sample into the cartridge 600. The lancet 614 can be used to pierce, puncture and/or cut a patient's tissue to cause bleeding, from which a blood sample can be taken.

The collected blood sample 622 can be collected in a blood sample chamber 620 of the cartridge 600. The blood sample chamber 620 can include a filter 624 to filter the blood sample 622. The filter 624 can be positioned within the blood sample chamber 620 of the cartridge 600 such that the blood sample chamber 620 is divided into a first and second portion, which are separated by the filter 624. The blood sample chamber 620 can include structural and/or chemical features to assist with the storage of the blood sample 622 and/or the analysis of the blood sample 622. Additionally, the blood sample chamber 620 can be located within the cartridge 600 to assist with and/or facilitate the analysis of the blood sample 622 using a reader.

A dilutant chamber 630 storing dilutant 632 can be included with the cartridge 600. The dilutant 632 within the dilutant chamber 630 can be mixed with the blood sample 622 in the blood sample chamber 620 and/or the cartridge 600 can include a mixing chamber 640 into which the dilutant 632 and blood sample 622, or portion(s) thereof, can be mixed before, during and/or after analysis of the blood sample 622. The dilutant 632 can include a fluid, or substance, to dilute the blood sample 622, a reagent, a chemical, a lysing agent, an anti-pathogen agent, an anti-foaming agent, and/or other fluid(s) that can be assist and/or facilitate the analysis of the blood sample 622. For example, foaming of the patient sample may compromise the quality of the analyzed data because the bubbles in a foamed patient sample affect the transmission of the light through the sample.

The cartridge 600 can include a physical disruptor 650 that can assist with the lyses of cells of the blood sample 622 in preparation for analysis. The physical disruptor 650 can include a mechanical, optical, and/or electrical system/device or portion thereof. In an example, a portion of a physical disrupter system or device can be included with the cartridge 600 and the other portion included on the reader and/or another external device. An example physical disruptor 650 can include a sonication horn that can direct sonic energy through the blood sample 622 to assist with lysing of the cells of the blood sample 622. The blood sample can undergo physical disruption in other ways as well, including employing maceration techniques and exposing the blood sample to distilled water or chemicals or any combination of desired disruption techniques.

The lysing can occur before or after dilution and/or other preparation of the blood sample 622. For example, the cartridge might include elements to transmit the maximum ultrasonic energy to the sample trough rods, cones or other shapes in contact with the blood sample.

The various chambers of the cartridge 600 can be interconnected and/or in fluid communication, allowing and/or facilitating the movement and/or transfer of fluid, with one or more of the chambers of the cartridge 600 and/or a connection to an external fluid source. The fluid communication between chambers can allow the blood sample 622, the dilutant 632 and/or other fluids to flow or be transferred from chamber to chamber(s) and can include passageways like flexible, rigid, and semi-rigid pipes and tubes. Flow control elements, such as valves, can be positioned along one or more of these passageways to regulate the fluid communication between chambers. The flow control elements can be manually actuated, such as by a reader or user applying pressure to the cartridge 600 or actuating the flow control element, or electrically actuated, such as by a signal from the reader or a user initiated signal or trigger.

Figure 7:
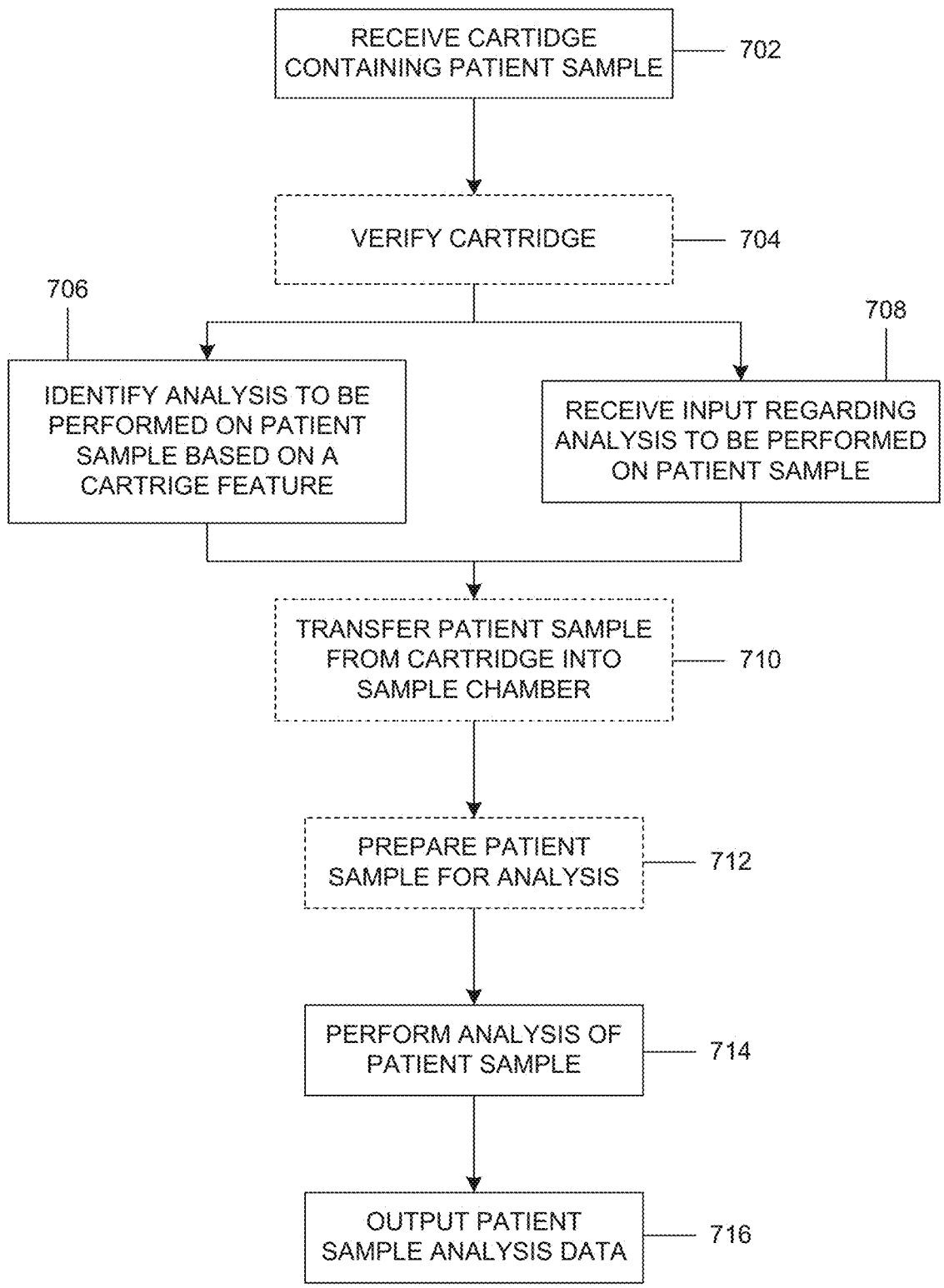
FIG. 7 illustrates an example patient sample analysis process.

FIG. 7 is an example patient sample analysis process 700 of a reader, processing circuitry, a device or system external to a reader and/or a combination thereof. The reader can receive a cartridge containing a patient sample 702, such as the insertion of a cartridge within a cartridge interface, the reader, and/or an external device connected to the reader or an external device or system. The cartridge can be optionally verified 704 to determine the validity of the cartridge and/or the patient sample within. The reader can then identify the analysis to be performed on the patient sample based on a cartridge feature 706, such as structural feature of the cartridge. That is, the reader can recognize or identify the cartridge type and a corresponding analysis that can be performed on the patient sample contained within. Alternatively, the reader can receive an input regarding the analysis to be performed on the patient sample 708. The input can include a user selecting an analysis, communication from an external system or device indicating the analysis performed or other input directing the reader to perform an analysis of the patient sample. Optionally, a portion of the patient sample can be transferred from the cartridge into a sample chamber 710 of the reader so that the patient sample can be analyzed within the sample chamber. Additionally, the patient sample can optionally be prepared for analysis 712, which can include lysing the sample, adding a dilutant to the patient sample or other preparation performed on or to the patient sample prior to patient sample analysis. The patient sample is then analyzed 714 by the reader and its systems and/or an external device or system. The patient sample analysis data is then output 716, such as transmitted to a reader and/or an external device or system. The output 716 can include interpretive data, such as the presence or absence of a disease, infection and/or condition within the patient sample, including detailed information, such as the type and degree of the disease, infection and/or condition.

Figure 8:
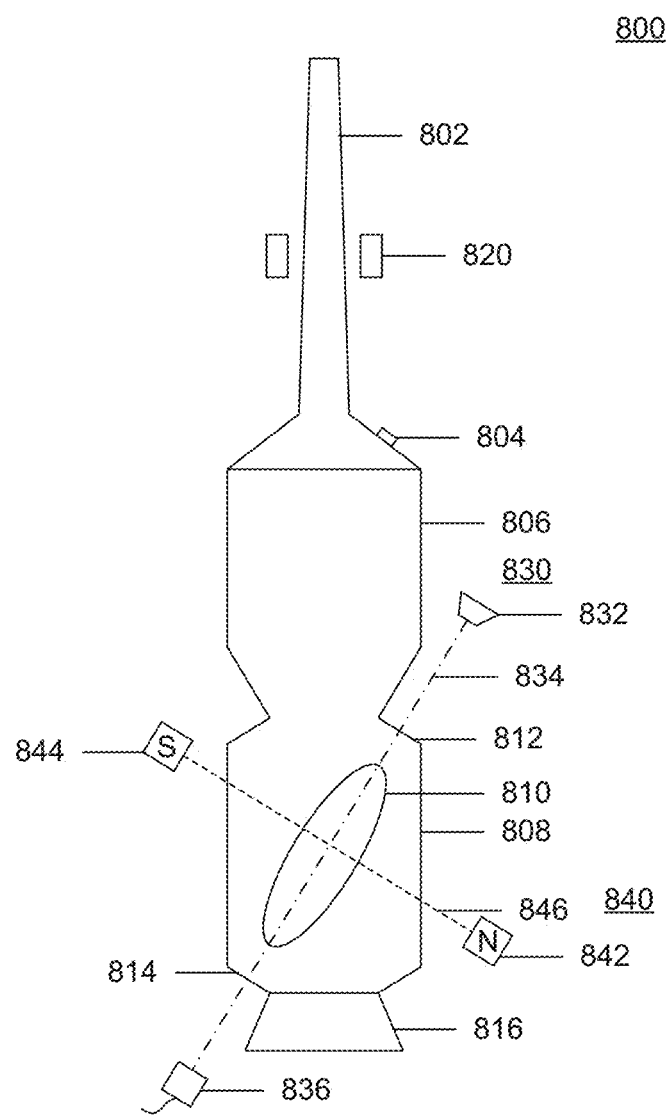
FIG. 8 is yet another example cartridge and magneto-optical detection components.

FIG. 8 illustrates an example cartridge 800 and various patient sample analysis devices/systems in relation to the cartridge 800. The patient sample analysis devices/systems can be included on a reader into which the cartridge 800 is inserted or received, the cartridge 800 can be inserted or received in a specific alignment or orientation in relation to the patient analysis devices/systems of the reader. Additionally, one or more portions of or a complete patient sample analysis device/system can be included with the cartridge 800.

A blood sample collector 802 can be included on the cartridge 800. The blood sample collector 802 can include a capillary or other tube, through which a patient's blood sample can be transferred into the cartridge 800. A capillary tube can use capillary action to draw the blood sample into the cartridge 800. A tube can be part of a pipette or pipette-like device or system of the cartridge 800, application and release of pressure on, or deformation of a portion of the cartridge 800 can cause a blood sample to be drawn through the blood sample collector 802, or portion thereof, due to a pressure differential between the surrounding environment and an internal portion or chamber of the cartridge 800.

The blood sample collector 802 can include a lancet or needle that can be used to cause a patient to bleed and/or with which to take the blood sample from the patient. The lancet or needle can be releasably or permanently affixed to the blood sample collector 802 or can extend and/or retract automatically and/or manually from the blood sample collector 802 to assist or facilitate the collection of a blood sample from a patient.

Alternatively, a patient blood sample can be obtained by other means or methods, and a portion of the patient blood sample can be transferred into the cartridge 800 through the blood sample collector 802 or through another input into the cartridge 800. For example, a blood sample can be drawn from a patient, for use in multiple analysis and/or diagnostic services, using a traditional method such as a needle and vacuum sample tube. From this collected blood sample, a portion of the sample to be analyzed using the cartridge 800 and/or a reader can be transferred into the cartridge 800 for analysis. In this manner, the patient is pierced a minimal number of times, drawing enough blood to run necessary diagnostic tests and analyses, including those using the reader and/or cartridge 800.

The cartridge 800 can include a vent 804 that can vent fluid or gas from within one or more chambers, or portions, of the cartridge 800. In some examples, the vent 804 is a one-way valve that facilitates fluid communication between the interior of the cartridge 800 and an external environment, such as the surrounding environment and the reader. Fluid communication means that the vent releases pressure from within the cartridge through the vent or other port. The vent 804 can be preset to a pressure threshold, if pressure inside the cartridge, a chamber or portion in fluid communication with the vent 804, exceeds the preset pressure threshold, the vent 804 opens to release fluid or gas from within the cartridge 804 until pressure on the vent 804 is reduced below the preset pressure threshold at which point the vent 804 closes.

The vent 804 can include a two-way valve to facilitate fluid communication between the interior of the cartridge 800 and an external environment, such as the surrounding environment and the reader. The fluid communication can include the exchange of a fluid or gas from external to the cartridge 800 to internal to the cartridge 800 through the vent 804. The two-way valve can include a preset pressure threshold that can trigger the opening of the valve. Once the pressure differential across the valve reaches the preset pressure threshold, the valve can open and allow the exchange of gas or fluid through the vent 804. For example, gas buildup within the cartridge 800, such as caused by mixing the blood sample and a dilutant, can be vented through the vent 804. In another example, a change in elevation of the cartridge 800, can cause a pressure differential between the interior of the cartridge 800 and the surrounding environment. The exchange of gas or fluid through the vent 804 can equalize the internal pressure of the cartridge 800, or portion thereof, with the external environment. In an example cartridge 800 including a two-way valve, the vent 804 can be used to transfer fluid, such as a dilutant, patient sample, or a mix of dilutant and patient sample, from the cartridge 800 to a reader or an external container or device.

The cartridge 800 can be divided into multiple portions 806 and 808. Each portion 806, 808 can include one or more internal chambers that can contain a fluid, such as a dilutant, blood sample, or a combination of the blood sample and dilutant. One or more internal chambers can also be empty allowing fluids to be introduced and/or mixed within in preparation for analysis and/or additional or alternate purposes. The internal chamber can be interconnected, such as by conduits or tubes, to allow fluid communication between the various chambers. Flow control devices can regulate flow of fluids and/or gases from one or more chamber to another chamber(s). Internal chamber(s) within the cartridge 800 can span across one or more portions of the cartridge 800. That is, a single internal chamber occupies space in both the first portion 806 and second portion 808 of the cartridge 800.

The cartridge 800 can include a sample chamber 810. The sample chamber 810 can be separate from the chamber in which the blood sample was originally stored within the cartridge 800. Additionally, the sample chamber 810 can include a filter that divides the sample into multiple portions. A first portion can receive the blood sample, which can then be passed through the filter, passively or actively and/or in response to an input, such as by a reader into which the cartridge 800 is inserted, into a second portion of the sample chamber 810 in which the analysis of the blood sample can be performed. The portions of the sample chamber can also be separated by a barrier that prevents and/or controls the flow of the blood sample between the portions of the chamber due to the geometry of the barrier, including openings disposed through the barrier. The barrier can be impermeable and block the flow of the blood sample between the portions of the sample chamber 810 until the barrier is selectively removed, such as by moving the barrier, including by inductively moving or controlling the barrier, or destroying the barrier, including puncturing the barrier, to allow the flow of the blood sample between the portions of the sample chamber 810. Alternatively, the barrier can be dissolvable, completely, or partially, to allow the flow and/or control the flow of the blood sample between the portions of the sample chamber 810. The barrier can also be semi-permeable to control the flow, such as a flow rate, of the blood sample between the portions of the sample chamber 810. In an example, a filter placed between the portions of the sample chamber 810 can be a semi-permeable barrier that controls the flow of the blood sample between the portions of the chamber 810.

In the example embodiment of FIG. 8, the sample chamber 810 is aligned along the pathway of incoming light 834. This arrangement maximizes the residence time or pathway through the sample within the sample chamber 810, which can assist in the efficiency and effectiveness of the analysis of the sample. As light is directed to transmit through the sample chamber 810, the sample chamber 810 can be constructed of a substantially transparent material that includes optical properties to assist with the analysis of the patient sample. Various cartridges 800 designed for various analyses can include differently or same shaped, oriented, and/or configured sample chambers 810, as shown in FIG. 8, and can be constructed of similar or different materials depending on the analyses to performed using the cartridge 800. The sample chamber 810 can include magnetic properties, such as being non-magnetic, that are based on the material and/or structure of the sample chamber 810. The magnetic properties of the sample chamber 810 can assist with or minimize a negative impact of the sample chamber 810 on the analysis of the sample within the sample chamber 810.

A collected sample can be stored within the sample chamber 810 or stored in a different chamber and then transferred into the sample chamber 810 in preparation for analysis. Additional materials or fluids can be added to the sample chamber 810 to mix with a sample in preparation for analysis. Additionally, the sample chamber 810 can be preloaded with various materials or fluids that can be mixed with the sample in preparation for analysis, including stabilizing or preserving the sample, assisting with lysing of the sample, reagents and/or other processes or procedures.

To assist with transmission of light 834 from a light source 832 through the sample chamber 810, the cartridge 800 can include windows or transparent portions 812, 814. The transparent portions 812, 814 can be transparent to the light 834 emitted from the light source 830. That is, the transparent portions 812, 814 can be substantially transparent, allowing visible light to transmit through the portions 812, 814, or the transparent portions 812, 814 can be effectively transparent to the light 834 emitted from the light source 830, which allows the emitted light 834 to pass through, but perhaps not visible light or some other select wavelength of light or range of wavelengths of light. Additionally, the transparent portions 812, 814 can be translucent rather than transparent.

In an example cartridge 800, the transparent portions 812, 814 can include optical properties to assist with the analysis of the patient sample within the sample chamber 810 by a reader, the cartridge 800 and/or other devices or systems. Example optical properties can include filtering of the incoming light 834, anti-reflection to minimize stray light, polarization of the incoming light 834 and other alteration and/or modification of the incoming light 834. Additionally, the transparent portions 812, 814 can include different optical properties. For example, the first transparent portion 812 can include an optical property, such as polarization, and the second transparent portion 814 can include a different optical property than the first transparent portion 812, including the absence of an optical property that affects light transmitted through the second portion 814.

The cartridge 800 can include a mechanical disruptor 816 to assist with preparation of a patient sample for analysis. The mechanical disruptor 816 can assist with the lysing of cells of the sample and can include a vibration element, a sonication horn or other disruptor or employ any other desired disruption technique like maceration or exposure to distilled water or chemicals or some combination of techniques. The sonication horn can direct incoming sonic energy, such as supplied by a reader or other device, through the sample within the sample chamber 810 to assist with lysing of the cellular component of the sample. The placement of the mechanical disruptor 816 is selected to lyse cells of the sample in an ideal, efficient, and/or effective manner. An example placement of the mechanical disruptor 816 is proximal to the cartridge 800 sample chamber 810, such as fitted against and/or contacting the sample chamber 810 to lyse the cells of the patient sample efficiently and/or effectively. In an example embodiment, a sonication horn of the cartridge 800 can directly contact the sample chamber 810 to direct sonic energy from a sonicator, such as a sonicator of a reader, through and cause lysing of the sample within.

A system or device external to the cartridge 800, or completely or partially included with the cartridge, can include a lysing laser 820. The lysing laser 820 can assist with lysing the cellular component of a patient sample. The positioning of the lysing laser 820 along the blood sample collector 802 allows the lysing laser 820 to lyse at least a portion of the blood sample as it is collected within the cartridge 800. Additionally, the blood sample within the cartridge 800 can be circulated or held within the blood sample collector 802 after collection, and exposed to the lysing laser 820 to assist with lysing at least a portion of the cellular component of the collected blood sample.

A light source and detector system 830 can be positioned external to and/or completely or partially included with the cartridge 800. The light source and detector system 830 can include the light source 832 which emits light 834 that can be detected by a light detector 836. The emitted light 834 can be transmitted through a blood sample within the cartridge 800 to assist with analysis of the blood sample. Light detection information, such as the amount of transmitted light and/or characteristics of the transmitted light, can be transmitted from the light detector 836 to a sample processing module of a reader and/or another device or system of the reader or one that is external the reader.

The light source 832 can include multiple different light emitting devices, including emitting light in a non-visible portion of the spectrum or in multiple portions of the spectrum, either simultaneously or sequentially. Example light sources 832 can include LED(s), lasers, and other light, or electromagnetic radiation emitting sources. The light detector 836 can be selected to detect light emitted from the light source 832, or from a portion of the electromagnetic radiation spectrum, such as visible light. Example light detectors 836 can include photodiodes, charge-coupled device, digital imaging sensor, a photovoltaic cell and/or other device that emits and/or alters a signal in response to incoming light. The information or data output from the light detector 836 can include detected light characteristic information, including detected light intensity.

The light source and detector system 830 and a magnet 840 can be part of an MOD that can be used to analyze the blood sample within the cartridge 800. The magnet 840 includes two opposing poles 842 and 844 that create a magnetic field 846. The two magnets might be attached with a yoke to increase the field. The magnetic field can affect a portion or component of the blood sample within the cartridge 800. Example magnets 840 capable of generating or having a magnetic field 846 can include one or more permanent magnets and one or more electromagnets, as discussed above. The magnet 840 can be moved proximal the cartridge 800 such that the blood sample within the cartridge 800 is effected by the magnetic field 846 and can be moved away from the cartridge 800 such that the magnetic field 846 effects the patient sample differently. Cycling an electromagnet can have a similar effect of subjecting the blood sample of the cartridge 800 to the presence, absence, and/or variance of a magnetic field 846. The magnets might include elements to focus the magnetic field.

The transparent portions 812 and 814 of the cartridge 800 can be arranged and/or oriented such that light 834 emitted from the light source 832 enters the cartridge 800 substantially, or nearly, perpendicular to the transparent portions 812 and 814. A small offset of the light entering the cartridge 800 can assist with preventing reflection of the incoming light back towards the light source 832, an example offset can include 5° from perpendicular. Arranging and/or orienting the transparent portions 812 and 814 substantially perpendicular to the incoming light 834 can reduce the reflection and/or refraction of the light 834 as it is transmitted through the transparent portion 812. The reduction in reflection and/or refraction of the entering light can reduce signal noise associated with the detection of the transmitted light by the light detector 836. This can assist with the efficiency and effectiveness of the patient sample analysis.

Figure 9:
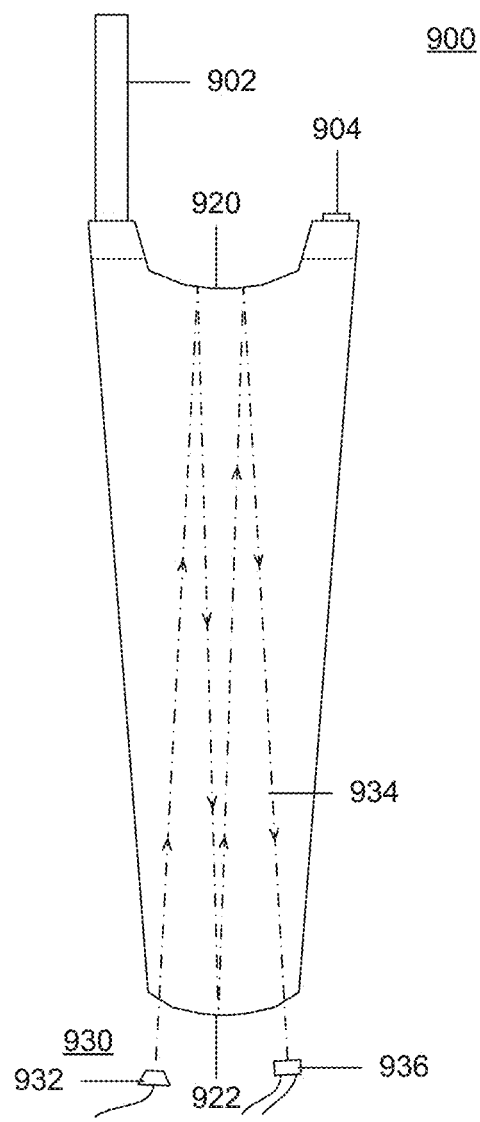
FIG. 9 is yet a further example cartridge and magneto-optical detection components.

FIG. 9 is a further example cartridge 900 and various sample analysis device and/or systems. The cartridge 900 can include a blood sample collector 902, a vent 904, reflective surfaces 920, 922, and, none, all or a portion of a light source and detector system 930. The reflective surfaces 920 and 922 reflect light repeatedly through a sample within the cartridge 900 which can increase the modification and/or alteration of light transmitted through the sample, the increased modification/alteration of the transmitted light can assist with the efficient and effective analysis of the blood sample. The cartridge is filled with the patient sample to a minimum fill point, which means a minimum volume of patient sample. In the example shown in FIG. 9, the minimum fill point creates a free surface of the fluid that is above the reflective surfaces. The portion of the cartridge with the reflective surface is concave and thus creates differing heights of the cartridge so that the minimum patient sample volume exceeds the height of the reflective surfaces, but it may or may not exceed the heights on either side of the reflective surfaces. Other geometries of the cartridge also can facilitate proper transmission paths for the light so that it travels entirely through the patient sample rather than extending above a free surface of the patient sample.

The cartridge 900 can include a blood sample collector 902 and vent 904, similar in structure and/or function to the blood sample collector 802 and vent 804 of FIG. 8. The blood sample collector 902 can be used to collect a blood sample of a patient within the cartridge 900 for analysis using the cartridge 900, a reader and/or other external device. The vent 904 can allow fluid communication, liquid or gas, between the interior of the cartridge 900 and an external environment, such as a reader or other external device. Additionally, the vent 904 can be used to equalize or reduce a pressure differential between the interior of the cartridge 900 and the exterior of the cartridge 900.

The reflective surfaces 920, 922 of the cartridge 900 can be interior to the cartridge 900 and exposed to the sample within. Alternatively, the reflective surfaces 920, 922 can be external the cartridge 900, separated from the sample within by a transparent or translucent membrane, element and/or portion of the cartridge 900 housing. Additionally, the internal reflective surfaces 920, 922 can be separated from the blood sample by a transparent or translucent membrane or coating. The reflective surfaces 920, 922 can include any reflective element that is attached or otherwise affixed or integrated with the cartridge 900 or can include a reflective coating or film of the cartridge 900 surface, making that portion of the cartridge 900 surface reflective. Additional reflective elements and materials can be used and arranged to reflect transmitted light 934 through the sample within the cartridge 900. The material of the reflective surfaces 920, 922 can be flexible, semi-flexible or rigid. The reflective surfaces 920, 922 can also be contoured or profiled to direct and/or aim the transmitted light reflected from the reflective surfaces 920, 922.

The light source and light detector system 930 includes a light source 932 that emits light 934 that transits through the blood sample within the cartridge 900. A light detector 936 receives the transmitted light and can quantify and/or characterize the received light, the light data can be transmitted to a sample module of a reader and/or an external device of system for use in analysis of the blood sample of the cartridge 900.

The tapered shape of the cartridge 900, as shown in FIG. 9, can mate and/or interface with a cartridge receptacle of a reader to properly place and/or orient the cartridge 900 within the reader in relation to the various analysis systems and/or elements of the reader. The proper position and/or orientation of the cartridge relative to the analysis systems can assist with the efficient and effective analysis of a patient sample within the cartridge 900. Additional systems and/or procedures of a reader, such as a physical disruptor and/or the addition of dilutant to a patient sample within the cartridge 900, can also be properly aligned, positioned, and/or performed relative to the cartridge 900 due to the geometry of the cartridge 900 and cartridge interface. The proper mating and/or interfacing of the cartridge 900 and the reader can allow or assist with the automation of an analysis of the patient sample within the cartridge 900.

Figure 10:
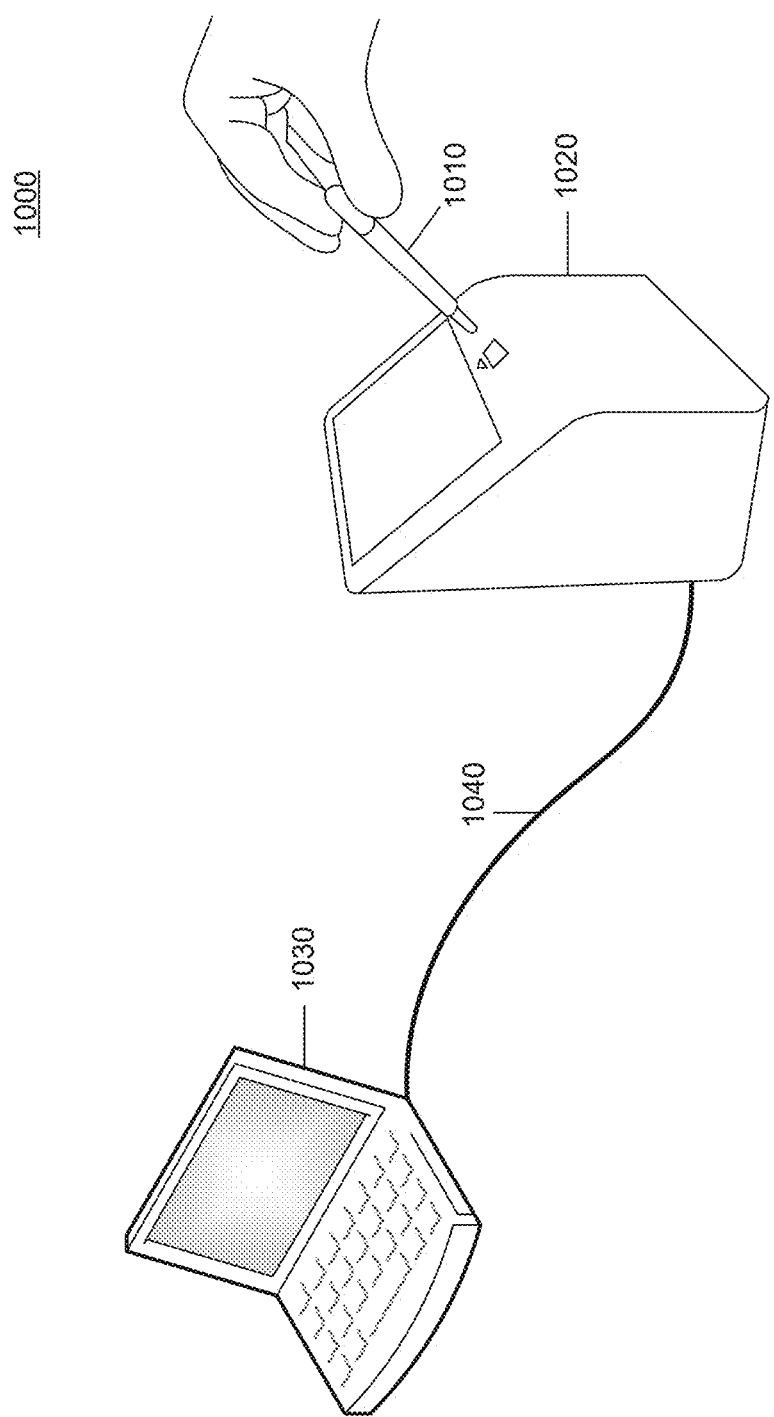
FIG. 10 illustrates a further example diagnostic system.

FIG. 10 illustrates an example diagnostic system 1000 that includes a cartridge 1010 and reader 1020, such as described herein, the reader connected 1040 to an external device 1030, such as a computing device, including a laptop, phone, tablet, a server, remote computer, or other external device. The connection 1040 between the reader 1020 and the external device 1030 can be a physical connection, such as a universal serial bus (USB) connector, such as shown in FIG. 10, or can be a wireless connection, such as an IR, Bluetooth® and/or WiFi electrical coupling, or a combination thereof. The connection 1040 allows communication between the reader 1020 and the external device 1030. In an example, the reader 1020 can perform analysis of a patient sample contained within the cartridge 1010, data from the various analysis systems and/or elements of the reader 1020 can be transmitted through the connection 1040 to the external device 1030 for processing. The external device 1030 can then display or transmit the processed results, or a portion thereof, to a user and/or can optionally transmit the processed results back to the reader 1020 for display and/or transmission of the analysis results, or a portion thereof, to the user. In a further example, the reader 1020 and external device 1030 can both process all or a portion of the patient sample analysis data. The external device 1030 can also control one or more aspects of the reader 1020, such as the analysis able to be performed by the reader 1020, authorized users of the reader 1020 or other aspects of the reader 1020 and its performance. Additionally, the external device 1030 can be in the proximity of the reader 1020, such as nearby, or can be remote from the reader 1020, such as in another room or in another location including in another country. The external device 1030 can communicate with and/or be connected to multiple readers and or other external systems, such as remote servers or databases.

Figure 11:
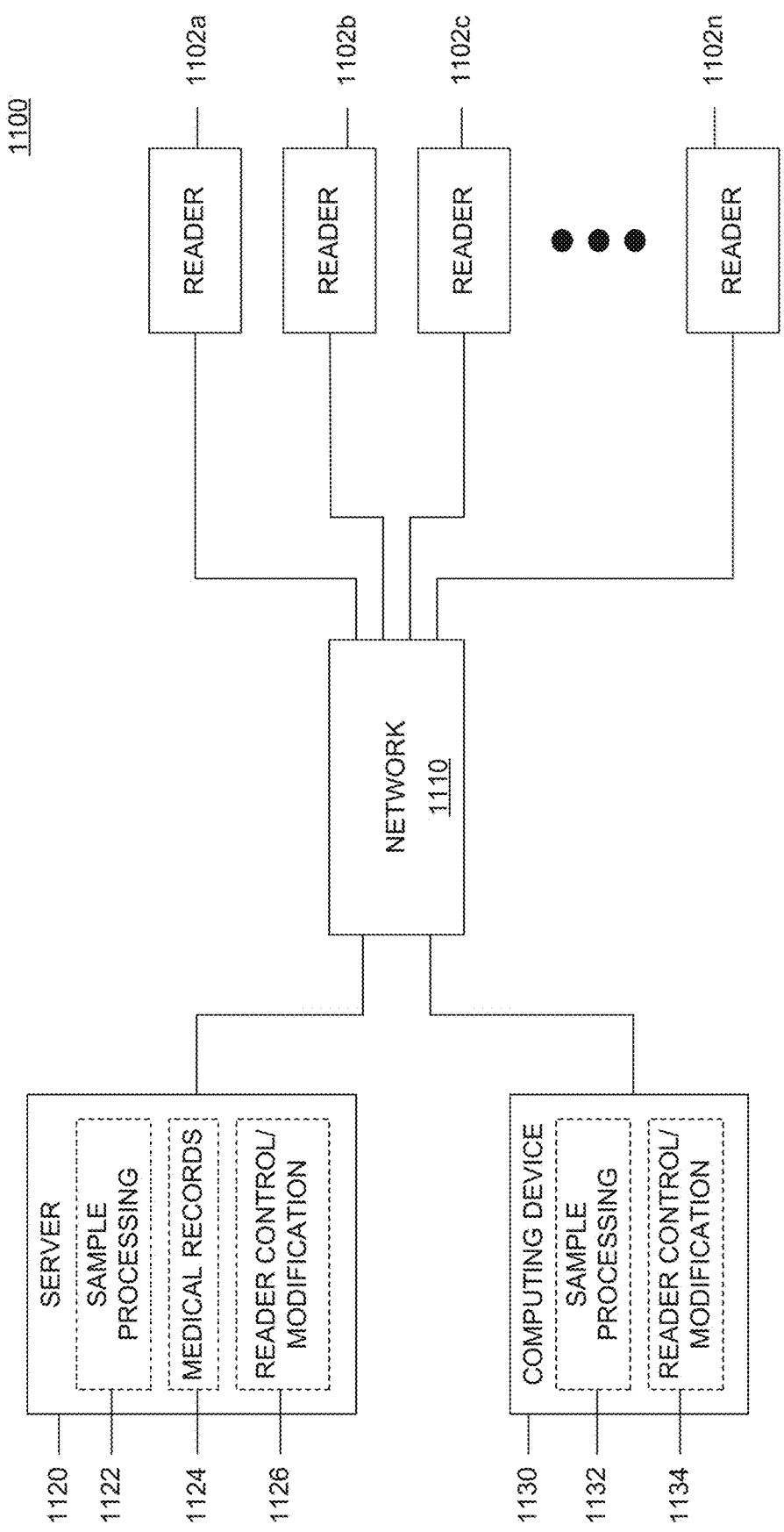
FIG. 11 is an example reader network.

FIG. 11 is an example reader network 1100. Various reader devices 1102*a*, 1102*b*, 1102*c* . . . 1102*n* are connected to external devices and/or systems, such as a server 1120 and/or computing device 1130, by a network 1110. The readers 1102*a*. 1102*b*, 1102*c* . . . 1102*n* can send and/or receive data, instructions, and other information to and/or from the external devices and/or systems 1120, 1130. The network 1110 can include physical and/or electronic connections to facilitate communication from the readers 1102*a*. 1102*b*, 1102*c* . . . 1102*n* to the external devices and/or systems 1120, 1130.

The readers 1102*a*, 1102*b*, 1102*c* . . . 1102*n* can be readers for use with a cartridge, as previously discussed, or can include other diagnostic and/or patient sample processing or storage devices. The readers 1102*a*, 1102*b*, 1102*c* . . . 1102*n* can communicate with the external devices and/or systems 1120, 1130 to transmit analysis data, receive analysis results and/or information, transmit status information, receive instructions, receive software updates and/or other communications or information exchanged between one or more readers 1102*a*, 1102*b*, 1102*c* . . . 1102*n* and/or external devices and/or systems 1120, 1130. The readers 1102*a*, 1102*b*, 1102*c* . . . 1102*n* can include a communication module to connect the reader 1102*a*, 1102*b*, 1102*c* . . . 1102*n* to the network 1110. The communication module can also be an external device to which the reader 1102*a*, 1102*b*, 1102*c* . . . 1102*n* is connected.

Additionally, the readers 1102*a*, 1102*b*, 1102*c* . . . 1102*n* can communicate with one another directly through a physical or wireless electronic connection. The connection between readers 1102*a*, 1102*b*, 1102*c* . . . 1102*n* can include intervening network devices, such as a router, or can be direct from one reader to one or more readers, such as an ad-hoc or local network. A reader can be designated as a primary device to transmit instructions to and receive data from other readers designated as secondary. Alternatively, no priority can be established between the readers 1102*a*. 1102*b*, 1102*c* . . . 1102*n*. The readers 1102*a*, 1102*b*, 1102*c* . . . 1102*n* can perform the same and/or different patient sample analyses.

The network 1110 can include wired connections, such as through an Ethernet connection, fiber optic connection, and/or other physical cable or connection. The network 1110 can also include electronic communication protocols, systems and/or methods, such a satellite communication, microwave communication. Wi-Fi, and Bluetooth®. The network 1110 can include multiple communication devices and/or protocols to facilitate communication between one or more readers 1102*a*, 1102*b*, 1102*c* . . . 1102*n* and/or external devices and/or systems 1120, 1130.

An example external device and/or system can include a server 1120 which can be remote from or local to the readers 1102*a*, 1102*b*, 1102*c* . . . 1102*n*. The server 1120 can include sample processing 1122, medical records 1124, reader control/modification 1126 and/or other information or systems to communicate with and/or receive information from a reader 1102*a*, 1102*b*, 1102*c* . . . 1102*n*.

Sample processing 1122 can include receiving data from a reader 1102*a*, 1102*b*, 1102*c* . . . 1102*n* and analyzing the data to perform the analysis of the patient sample. Remote processing of the patient sample data can reduce the computing burden of the reader 1102*a*, 1102*b*, 1102*c* . . . 1102*n*. Additionally, remote processing can allow for more effective and efficient processing by consolidating the analysis in one or more locations, such as the server 1120. Consolidation can allow for the use of computer learning and/or larger databases for use in analysis of the patient sample. Such data aggregation can be used to map and/or research trends, map outbreaks, institute control procedures to contain an infection and/or various other data analyses. Additionally, updating the analysis process can be required at fewer locations, the server 1120, rather than on each individual reader 1102*a*, 1102*b*, 1102*c* . . . 1102*n*.

The server 1120 can also include medical records 1124. The analysis performed by the server 1120 or reader 1102*a*, 1102*b*, 1102*c* . . . 1102*n* can be appended to the relevant patient medical record 1124. Medical records 1124 can be stored on the server 1120 or on an external device and/or system, to which the server 1120 and/or reader 1102*a*, 1102*b*, 1102*c* . . . 1102*n* can communicate the necessary data and/or analysis. The sample processing 1122 can also access the medical records 1124 to perform pattern analysis to determine trends, clusters, and potential preventative measures to reduce impact of a disease and/or condition in a certain region, population and/or demographic. Further, the pattern analysis can be used to determine spread of a disease and/or condition. This can allow resources to be dedicated in response to an outbreak or potential outbreak of a disease and/or condition.

The server 1120 can also include reader control/modification 1126. Reader control/modification 1126 can include reader calibration information, software updates to the reader 1102*a*, 1102*b*, 1102*c* . . . 1102*n*, ensuring proper and/or authorized use of a reader 1102*a*, 1102*b*, 1102*c* . . . 1102*n* and/or other control or operational changes to a reader 1102*a*, 1102*b*, 1102*c* . . . 1102*n*. Centralizing reader control/modification 1126 can assist with proper reader 1102*a*, 1102*b*, 1102*c* . . . 1102*n* usage, maintenance and/or functionality to provide efficient and effective patient sample analysis using a reader 1102*a*, 1102*b*, 1102*c* . . . 1102*n*.

Another example external device and/or system can include a computing device 1130. The computing device 1130, such as a mobile phone, computer, tablet, or other device, can be connected to one or more readers 1102a, 1102b, 1102c . . . 1102n through the network 1110. The computing device 1130 can receive information from the reader 1102a, 1102b, 1102c . . . 1102n and perform some or all the sample processing and/or analysis 1132, based on the received information. Additionally, the external device 1130 can act as an output to which the reader 1102a, 1102b, 1102c . . . 1102n transmits results, data and/or information regarding the patient sample analysis. As with the server, discussed above, the computing device 1130 can also include reader control/modification 1134. The reader control/modification 1134 can provide an input through which instruction to a reader 1102a, 1102b, 1102c . . . 1102n can be entered. Additionally, the reader control/modification 1134 can include calibration and/or maintenance data and/or processes a user and/or reader 1102a, 1102b, 1102c . . . 1102n can perform to assist with maintenance and/or calibration of the reader 1102a, 1102b, 102c . . . 1102n. The proper functioning and calibration of the reader 1102a, 1102b, 1102c . . . 1102n can assist with the efficient and effective analysis of patient samples. Additionally, the computing device 1130 can communicate with the server 1120 using the network 1110 or other communication means, systems and/or processes.

In an example, the computing device 1130 can store and/or transmit data from one or more readers 1102a, 1102b, 1102c . . . 1102n to the server 1120. The data transmission can be in real-time or can be stored and transmitted when convenient or the computing device 1130 is again connected to a network 1110. Additionally, the computing device 1130 can transmit the results of an analysis to a patient and/or a patient representative, such as a patient's physician. As with transmission of the data from the reader, the transmission of the patient analysis can be performed in real-time or at a later time, such as when the computing device 1130 is again connected to a network 1110

The invention claimed is:

1. A point-of-care diagnostics system, comprising:
a cartridge having:
a blood sample chamber structured to receive and store a patient blood sample,
a dilutant chamber structured to store a pre-loaded dilutant, and
a barrier separating the blood sample and dilutant chambers, the barrier is structured to, upon actuation, automatically release the dilutant to be mixed with the patient blood sample to form a diluted sample within the cartridge;
a reader having:
a cartridge receptacle shaped to receive the cartridge;
a magnetic field source structured to apply either a high magnetic field or a low magnetic field to at least the blood sample chamber of the cartridge when the cartridge is received within the cartridge receptacle;
a light source positioned to selectively transmit light through the diluted sample when the cartridge is received in the cartridge receptacle;
a light detector positioned to sense one or more characteristics of the light transmitted through the diluted sample and to generate light detection data based, at least in part, on the sensed one or more characteristics of the light transmitted through the blood sample;
a processor electrically coupled to the light detector and programmed to:
cause the light detector to sense the one or more characteristics of the light transmitted through the diluted sample and to generate the light detection data at a first time when the high magnetic field is applied or the low magnetic field is applied to the blood sample chamber of the cartridge;
after the light detection data is generated at the first time, cause the magnetic field source to apply the high magnetic field or the low magnetic field, whichever was not applied at the first time, to the blood sample chamber;
cause the light detector to sense the one or more characteristics of the light transmitted through the diluted sample and to generate the light detection data at a second time when the high magnetic field or the low magnetic field is applied, whichever was not applied at the first time;
determine a difference in a value of the light detection data between the first time and the second time;
receive the difference in the value of the light detection data;
analyze the received difference in the value of the light detection data to identify whether at least one compound that is sensitive to the applied magnetic field is present in the diluted sample;
generate interpretative data that indicates presence of the compound in the diluted sample based, at least in part, on the difference in the value of the analyzed light detection data; and
output the interpretative data.

2. The point-of-care diagnostics system of claim 1, further comprising an integrated blood sample collector that includes one or more of:
a moveable lancet that, upon actuation, is structured to automatically extend to collect the patient blood sample, and, after the blood sample is collected, automatically retract into the cartridge,
a retractable lancet that is structured to remain static to collect the blood sample and, after collecting the blood sample, retracts into the cartridge,
or a fixed lancet.

3. The point-of-care diagnostics system of claim 2, wherein the barrier includes one or both of a passive and an active mechanism that, when actuated, automatically causes the release of the dilutant to mix with the patient blood sample.

4. The point-of-care diagnostics system of claim 3, wherein the cartridge further includes a mixing chamber in which the pre-loaded dilutant is mixed with the patient blood sample.

5. The point-of-care diagnostics system of claim 1, further comprising a physical disruption component structured to cause lysing of one or more compounds in the blood sample.

6. The point-of-care diagnostics system of claim 1, wherein the light source is positioned to transmit light through a portion of the blood sample chamber with the diluted sample.

7. The point-of-care diagnostics system of claim 1, wherein the blood sample chamber is further structured to store one or both of a pre-loaded anti-pathogen and a pre-loaded anti-foaming compound.

8. The point-of-care diagnostics system of claim 1, wherein the cartridge has a vent structured to maintain an internal pressure of the blood sample chamber at or near a pressure of an ambient environment surrounding the cartridge.

9. The point-of-care diagnostics system of claim 1, wherein the light source is positioned to transmit light through the diluted sample at a controlled angle with respect to surfaces of the cartridge through which the light enters and exits the cartridge.

10. The point-of-care diagnostics system of claim 1, further comprising one or both of:
an actuator that is positioned to be automatically actuated when the cartridge is received in the cartridge receptacle, and
a cartridge sensor that is configured to detect the presence of the cartridge within the cartridge receptacle, the cartridge sensor electrically coupled to the processor and configured to transmit cartridge data indicating the presence of the cartridge in the cartridge receptacle to the processor.

11. The point-of-care diagnostics system of claim 1, wherein the processor is further programmed to cause the light detector to sense the relative intensity of the transmitted light a single time or multiple times, and if the light detector is configured to sense the relative intensity multiple times, then the processor causes the light detector to sense the relative intensity of the transmitted light over a period of time during which the light detector repeatedly detects the relative intensity at set intervals or randomly throughout the period of time.

12. The point-of-care diagnostics system of claim 1, wherein the processor is further programmed to automatically generate the interpretative data that indicates presence of the compound in the diluted sample.

13. The point-of-care diagnostics system of claim 1, wherein the processor is further programmed to automatically transmit the output interpretive data to a display.

14. The point-of-care diagnostics system of claim 1, wherein the processor is further programmed to receive user input requesting the interpretive data and, based on the received user input, is also further configured to automatically transmit the output interpretive data to the display.

15. The point-of-care diagnostics system of claim 13, wherein the display is integrated into the reader.

16. The point-of-care diagnostics system of claim 13, wherein the processor is further programmed to transmit the output interpretive data to the display and the display is integrated into a remote computing device.

17. The point-of-care diagnostics system of claim 1, wherein a portion or all of one or both of the cartridge and the reader are temperature-controlled.

18. The point-of-care diagnostics system of claim 1, further comprising an integrated power source in the reader, the power source electrically coupled to the light detector and the processor.

19. The point-of-care diagnostics system of claim 1, further comprising an output configured to receive the interpretative data and the output is integrated within the reader and includes one or more of a display, a visual indicator, an audible indicator, and a computing element remote from the reader.

20. The point-of-care diagnostics system of claim 19, wherein the remote computing element is wirelessly connected to the reader or is connected to the reader via a wired electrical connection.

21. The point-of-care diagnostics system of claim 1, wherein the processor is integrated within the reader.

22. The point-of-care diagnostics system of claim 1, wherein the processor includes processing circuitry that is wirelessly connected to the light detector and is integrated partially or entirely in a computing element remote from the reader.

23. The point-of-care diagnostics system of claim 1, wherein the processor includes processing circuitry and at least a portion of the processing circuitry is integrated within the cartridge.

24. The point-of-care diagnostics system of claim 1, further comprising an actuator that, when actuated, indicates that the cartridge is received within the cartridge receptacle, and that the actuator is electrically coupled to the processor, wherein the processor is further programmed to cause the light source to begin transmitting light through the patient blood sample when the processor receives a data transmission that the cartridge is received within the cartridge receptacle.

25. The point-of-care diagnostics system of claim 1, wherein the processor is further programmed to measure a relative intensity of the light transmitted through the diluted sample, and to automatically generate the interpretive data to include the measurement of the relative intensity.

26. The point-of-care diagnostics system of claim 1, wherein the processor includes reader processing circuitry and remote computing element processing circuitry, wherein
the reader processing circuitry is configured to receive the light detection data, and
the remote computing element processing circuitry configured to the analyzing, generating, and outputting steps, wherein the generating and outputting steps are performed automatically.

27. The point-of-care diagnostics system of claim 26, wherein the remote computing element processing circuitry is further configured to transmit the output interpretive data to one or both of a display integrated in the reader and a display integrated in the remote computing system.

28. The point-of-care diagnostics system of claim 1, wherein the processor is further programmed to automatically analyze the light detection data to measure the amount of the compound that is present in the diluted sample and to automatically generate the interpretive data to include the measured amount of the compound.

29. The point-of-care diagnostics system of claim 1, wherein the processor is further programmed to correlate the one or more sensed characteristics of the light transmitted through the blood sample with a level of hemozoin.

30. The point-of-care diagnostic system of claim 1, wherein the magnetic field source is a pair of permanent magnets.

31. The point-of-care diagnostic system of claim 1, wherein, the high magnetic field is applied at the first time and the low magnetic field is applied at the second time.

32. The point-of-care diagnostic system of claim 1, wherein the low magnetic field is applied at the first time and the high magnetic field is applied at the second time.

33. The point-of-care diagnostic system of claim 1, wherein the interpretative data is output automatically.

34. The point-of-care diagnostic system of claim 1, wherein the interpretative data is based on the values of the analyzed light detection data when applying the high and low magnetic fields at the first time and the second time, respectively.

35. The system of claim 1, further comprising a mechanical lysing element structured to mechanically lyse the patient blood sample.

36. The system of claim 35, wherein the mechanical lysing element is structured to mechanically lyse the patient blood sample without physically contacting the patient blood sample.

37. The system of claim 35, wherein the mechanical lysing element is structured to mechanically lyse the patient blood sample from a position external to the cartridge.

38. The system of claim 1, wherein the cartridge is one or both of a single-use cartridge and a disposable cartridge.

39. The system of claim 1, wherein the actuation of the barrier is manual or automatic.

40. The system of claim 1, wherein the barrier is semipermeable.

41. The system of claim 1, wherein the barrier is impermeable.

42. The system of claim 1, wherein the barrier is a physical barrier at least partially bisecting the cartridge to form the blood sample and dilutant portions.

43. The system of claim 1, wherein the barrier is destroyable.

44. The system of claim 43, wherein the barrier is puncturable or dissolvable.

45. The system of claim 1, wherein the barrier is moveable.

\* \* \* \* \*

UNITED STATES PATENT AND TRADEMARK OFFICE
CERTIFICATE OF CORRECTION

PATENT NO. : 10,768,166 B2
APPLICATION NO. : 15/599368
DATED : September 8, 2020
INVENTOR(S) : Peter Galen et al.

It is certified that error appears in the above-identified patent and that said Letters Patent is hereby corrected as shown below:

On the Title Page

In the Abstract:
Column 1, Line 1, item (57), "diagnostic" should be --diagnostics--.

In the Claims

Claim 30, Column 36, Line 48, "diagnostic" should be --diagnostics--.

Claim 31, Column 36, Line 51, "diagnostic" should be --diagnostics--.

Claim 32, Column 36, Line 54, "diagnostic" should be --diagnostics--.

Claim 33, Column 36, Line 58, "diagnostic" should be --diagnostics--.

Claim 34, Column 36, Line 60, "diagnostic" should be --diagnostics--.

Signed and Sealed this
Third Day of May, 2022

Katherine Kelly Vidal
*Director of the United States Patent and Trademark Office*